United States Patent [19]
Travis et al.

[11] Patent Number: 5,447,914
[45] Date of Patent: Sep. 5, 1995

[54] ANTIMICROBIAL PEPTIDES

[75] Inventors: James Travis, Athens; William M. Shafer, Stone Mountain, both of Ga.; Neelesh Bangalore, Gaithersburg, Md.; Jan Pohl, Doraville, Ga.

[73] Assignees: Emory University, Atlanta; University of Georgia Research Foundation, Inc., Athens, both of Ga.

[21] Appl. No.: 956,848

[22] Filed: Oct. 2, 1992

Related U.S. Application Data

[63] Continuation-in-part of Ser. No. 541,635, Jun. 21, 1990, abandoned.

[51] Int. Cl.[6] .................... A61K 38/00; C07K 7/00; C07K 7/08; C07K 7/06
[52] U.S. Cl. .................... 514/16; 530/326; 530/328; 530/329; 514/14; 514/15
[58] Field of Search .............. 514/16; 530/328, 326, 530/329

[56] References Cited

PUBLICATIONS

Miyasaki and Bodeau (1991) J. Clin. Invest 87:1585–1593.
Wasiluk et al. (1991) Infect. Immun. 59:4193–4200.

*Primary Examiner*—Jill Warden
*Assistant Examiner*—S. G. Marshall
*Attorney, Agent, or Firm*—Greenlee and Winner

[57] ABSTRACT

Peptides which exhibit antimicrobial activity comparable to certain known antibiotics are provided. These peptides are related in sequence to amino acid sequences within Cathepsin G. A broad spectrum bactericidal peptide disclosed herein is RPGTLCTVAGWGRVSMRRGT (SEQ ID NO:22). It is active against *Pseudomonas aeruginosa*, *Neisseria gonorrhoeae* and *Staphylococcus aureus*. RRENTQQHITARRAIRHPQY (SEQ ID NO:19) and GKSSGVPPEVFTRFVSSFLPWIRTTMR (SEQ ID NO:20) also exhibited potent activity against *P. aeruginosa* strains, including clinical isolates. IIGGR (SEQ ID NO:1) and IVGGR (SEQ ID NO:2) act against both gram-negative and gram-positive bacterial strains. HPQYNQR (SEQ ID NO:3) and certain related peptides are also active against both gram-negative and gram-positive bacteria, including, but not limited to, strains of *Escherichia coli*, *Neisseria gonorrhoeae*, *Staphylococcus aureus*, *Capnocytophage sputigena* and *Pseudomonas aeruginosa*. The peptides of the present invention will be useful in pharmaceutical compositions useful in the treatment of prophylaxis of infections.

4 Claims, 11 Drawing Sheets

```
1                                                     *                61
IIGGRESRPHSRPYMAYLQIQSPAGQSRCGGFLVREDFVLTAAHCWGSNINVTLGAHNIDRRENTQ

80        *                                    117
QHITARRAIRHPQYNQRTIQNDIMLLQLSRRVRRNRNVNPVALPRAQEGLRPGTLCTVAGWGRVS

136                                   #   ###*                    #
MRRGTDTLREVQLRVQRDRQCLRIFGSYDPRRQICVGDRRERKAAFKGDSGGPLLCNNVAHGIVS

#           223
YGKSSGVPPEVFTRVSSFLPWIRTTMR
```

FIG. 8

```
                         Hydrophilic      0    Hydrophobic
Residue   Score    Avg.  -------------------:-------------------
117 R    -4.50   -2.167          *               .
118 P    -1.60   -0.900               *          .
119 G    -0.40    0.900                          . *
120 T    -0.70    1.867                          .   *
121 L     3.80    1.867                          .   *
122 C     2.50    2.000                          .    *
123 T    -0.70    1.767                          .   *
124 V     4.20    1.867                          .   *
125 A     1.80    0.167                         *
126 G    -0.40   -0.567                    *     .
127 W    -0.90   -1.933            *             .
128 G    -0.40   -0.233                      * .
129 R    -4.50   -0.367                     *    .
130 V     4.20    1.767                          .     *
131 S    -0.80   -1.133               *          .
132 M     1.90   -2.367          *               .
133 R    -4.50   -3.133       *                  .
134 R    -4.50   -1.867            *             .
135 G    -0.40   -0.550                      *   .
136 T    -0.70   -0.700                      *   .
```

FIG. 9

|                     | 117                    | 136 |
|---------------------|------------------------|-----|
| Cathepsin G         | R P G T L C T V A G W G R V S M R R G T |
| Human granzyme B    | K . . Q T . S . . . . . Q T A P L G K S |
| Mouse Granzyme B    | K . . D V . Y . . . . . . M A P M G K Y |
| CAP 37              | E A . . R . Q . . . . . S Q - R S G . R |
| Human elastase      | G N . V Q . L A M . . . L L G R N . . I |
| Proteinase 3        | P H . . Q . L A M . . . . . G A H D P P |
| Bovine chymotrypsin | A A . . T . V T T . . . L T R Y T N A N |

FIG. 10

ANTIMICROBIAL PEPTIDES

GOVERNMENT RIGHTS

This invention was made, in part, with funding from the National Institutes of Health and from the Department of Veterans Affairs Research Service. The United States Government may have certain rights in this invention.

CROSS-REFERENCE TO RELATED APPLICATIONS

This application is a continuation-in-part of U.S. Ser. No. 07/541,635, filed Jun. 21, 1990, now abandoned, which is incorporated by reference herein.

TECHNICAL FIELD

The field of this invention is the area of antimicrobial peptides with activity against a broad range of Gram-negative and Gram-positive bacteria and fungi. The antimicrobial peptides of this invention are useful for inhibiting microbial growth and in pharmaceutical compositions for treatment or prevention of infections and for the treatment and/or prevention of gingivitis.

BACKGROUND OF THE INVENTION

Microbes which invade the human body are challenged by several defense mechanisms. The nature of the defense mechanisms which any given microbe faces depends on the genetic makeup and the physiologic state of the host as well as the portal of entry of the invading microorganism.

Host defenses include mechanical factors and chemical factors. Mechanical factors which help protect epithelial surfaces include the washing action of bodily fluids, including tears, saliva and urine, trapping on mucous layers, removal by cilia and elimination by coughing, sneezing or desquamation. A further mechanical defense is offered by the physical integrity of the skin, although mucous membranes can be penetrated by some pathogens.

Chemical defense factors include the acidity of gastric secretions, unsaturated fatty acids on the skin which kill certain bacterial species, lysozyme in tears, saliva and nasal secretions, iron-binding proteins at the mucosal surface, transferrin in serum, and spermine in semen. Secretions of the mucous membranes also contain antibodies, especially those of the IgA class. Microbial antagonism between different potentially pathogenic bacteria, fungi and yeast strains occurs at the level of competition for nutrients and through the production of inhibitory substances; this antagonism affords further protection to the host.

If the barriers of the skin or mucous membranes are crossed, immunological factors (e.g., antibodies) which are specific to the microorganism as well as nonspecific cellular defenses come into play. In addition, there are some chemical factors which also play a role in host defense, especially transferrin, which chelates available iron on which microorganisms are dependent.

Nonspecific cellular defenses in the form of phagocytic white blood cells from local tissues and the bloodstream respond to an invading microbe. Polymorphonuclear leukocytes (PMNs) actively phagocytize particulates such as bacterial or fungal cells. PMNs are the first class of phagocytic cells recruited to the site of infection or inflammation. The PMNs contain azurophilic or primary granules, which contain lysosomal proteases, myeloperoxidase, lysozyme and certain antimicrobial proteins. Secondary granules within these cells contain alkaline phosphatase, lactoferrin and lysozyme. Stores of glycogen within the PMNs provides for energy through glycolysis so that the cell can function in an anaerobic environment.

Adherence of a particle to the surface of a phagocytic cell initiates phagocytosis; the particle enters the cytoplasm in a phagocytic vacuole. This triggers a respiratory burst and the generation of microbicidal metabolites; the primary granule fuses with the phagocytic vacuole to form a digestive vacuole called the phagolysosome. Intracellular killing of the ingested microorganism occurs as a result of oxygen-dependent and oxygen-independent mechanisms. The oxygen-dependent bactericidal halogenating system uses granule myeloperoxidase, hydrogen peroxide and chloride ion to kill bacteria and viruses via either halogenation of cellular or viral constituents or via reactive oxygen intermediates. Oxygen-dependent killing can also proceed by direct reduction of molecular oxygen via the cytochrome b-oxidase system (reviewed by Orkin (1989) Ann. Rev. Immunol. 7:277–308). Oxygen-dependent killing mechanisms are reviewed by Beaman and Beaman (1984) Ann. Rev. Microbiol. 38:27–48.

The primary granules contain three major groups of antibacterial proteins. The first group includes catalytically active proteins which are only weakly antibacterial when tested individually in purified form. Examples from this group include lysozyme, elastase and collagenase. These enzymes probably participate in the digestion of microorganisms killed by other mechanisms, but elastase, for example, is believed to potentiate killing by the halogenating system. The second category of granule proteins includes those with catalytic activity and bactericidal activity which is independent of the catalytic activity. An example is the chymotrypsin-like neutral protease of human neutrophils. A third group contains bactericidal members which lack known catalytic activity; such a protein class has been purified from rabbit neutrophils. Included in this class are defensins and cationic antibacterial proteins.

Some cationic antibacterial proteins are of relatively high molecular weight (greater than about 25 kDa) and kill certain Gram negative bacteria such as *Escherichia coli*, *Salmonella typhimurium* and *Pseudomonas aeruginosa* by damaging the cytoplasmic membrane, leading to increased membrane permeability. Human bactericidal/permeability increasing protein (BPI) is a strongly basic protein with molecular weight of about 59 kDa. It is believed that when bound to the outer membrane of susceptible bacterial cells, hydrophobic channels through the outer envelope are exposed, and as a secondary effect, there is a selective activation of autolytic enzymes including phospholipase and peptidoglycan hydrolases. Gram positive bacteria, certain Gram negative bacteria and fungi are not affected by BPI in vitro.

Low molecular weight cationic proteins (10 kDa to 25 kDa) have been reported which inhibit the multiplication of such Gram positive bacteria as *Staphylococcus aureus* (Root and Cohen (1981) Rev. Infect. Dis. 3:565–598). In addition, cationic proteins with fungicidal activity have been identified in alveolar macrophages. It is believed that cationic proteins are most efficient in killing phagocytized microorganisms in combination with other microbicidal defense mechanisms (Elsbach and Weiss (1983) supra).

Generally defensins are relatively small polypeptides of about 3-4 kDa, rich in cysteine and arginine. Gabay et al. (1989) Proc. Natl. Acad. Sci. USA 86:5610-5614, used reverse phase HPLC to purify 12 major polypeptides from the azurophil granules of human PMNs; purified proteins were analyzed individually for antimicrobial activity and for N-terminal amino acid sequence. A 4 kDa defensin (HNP-4) and a 29 kDa polypeptide named azurocidin were purified and shown to possess broad spectrum antimicrobial activity. Defensins as a class have activity against some bacteria, fungi and viruses. They are also reported to have cytotoxic activity against transformed cells. Selsted et al. (1985) J. Clin. Invest. 76:1436-1439, presents a sequence comparison of human and rabbit defensins. The defensins are believed to have molecular conformations stabilized by cystine infrastructure, which are essential for biological activity.

Granzymes are a family of serine proteases in the granules of cytolytic lymphocytes. Proteolytic enzymes are believed to function in cell-mediated cytoxicity; some of the genes have been cloned, and sequence information is available. Within the granzyme family there is at least 38% amino acid sequence identity. Human lymphocyte protease has 73% amino acid sequence identity to mouse granzyme B (Jenne and Tschopp (1988) Immunol. Reviews 103:53-71).

Cathepsin G (Cat G) is a granule protein with chymotrypsin-like activity; it is also known as chymotrypsin-like cationic protein. Cat G (Odeberg and Olsson (1975) J. Clin. Invest. 56:1118-1124) and three other mutually homologous polypeptides called defensins are active against a broad spectrum of gram positive bacteria, gram negative bacteria and fungi (Shafer et al. (1986) Infect. Immun. 54:184-188; Shafer et al. (1988) Infect. Immun. 56:51-53; Drazin and Lehrer (1977) Infect. Immun. 17:382-388; Ganz et al. (1986) Semin. Respir. Infect. 1:107-117). Sensitive bacteria include *Capnocytophaga sputigena, Escherichia coli, Listeria monocytogenes, Neisseria gonorrhoeae, Pseudomonas aeruginosa* and *S. aureus*. All of these pathogens, with the notable exceptions of *P. aeruginosa* and *C. sputigena*, are only sensitive to both enzymatically-active and -inactive cathepsin G (Miyasaki and Bodeau (1991) J. Clin. Invest 87:1585-1593; Wasiluk et al. (1991) Infect. Immun. 59:4193-4200 and Table 11 herein). *P. aeruginosa* and *C. sputigena* are only sensitive to enzymatically-active cathepsin G. It is not clear, however, if cathepsin G-killing of these two pathogens requires degradation of bacterial proteins or whether an intact active site is needed to align antibacterial domains of cathepsin G with the bacterial target.

Gabay et al. (1989) supra, has reported antibacterial activities of a number of proteins isolated from human PMNs, including cathepsin G and elastase, and has given the amino terminal sequence of these and other proteins. The N-terminal five amino acids of elastase and Cat G are identical; further sequences have significant relatedness. Cat G also exhibits significant sequence similarity to chymotrypsin, which is not known to exhibit antimicrobial activity similar to that of Cat G.

The sequence of human Cat G is known, and the gene has been cloned from human leukemic cell line U937 (Salvesen et al. (1987) Biochemistry 26:2289-2293). Sequence analysis of the cDNA revealed significant sequence identity to rat mast cell proteinase (47%) and to an activated mouse cytotoxic lymphocyte product (56%).

Another class of antimicrobial polypeptides are those known as magainins; at least five proteins can be isolated from the skin of the African clawed frog (*Xenopus laevis*). The natural proteins are active against a broad range of microorganisms including bacteria, fungi and protozoans (Zasloff (1987) Proc. Natl. Acad. Sci. USA 84:5449-5453). The broad spectrum antimicrobial activity is present in synthetic peptides and in certain truncated analogs of the natural proteins. Derivatives of about 19 to about 23 amino acids have antibacterial activity as measured using *Escherichia coli*. In the protozoan *Paramecium caudatum* treated with the magainin peptides, there is disruption of membrane functions. The configurations of the bioactive peptides can be modeled as amphiphilic alpha-helices and are sufficiently long to span a lipid bilayer. (Zasloff et al. (1988) Proc. Natl. Acad. Sci. USA 85:910-913). Spanning a lipid bilayer is believed to require at least 20 amino acid residues in an alpha-helical configuration (Kaiser and Kennedy (1987) Ann. Rev. Biophys. Chem. 16:562-581). The sequence of a representative magainin peptide is GIGKFLHSAKKFKAFVGEIMN (SEQ ID NO:48) (Zasloff et al. (1988) supra).

SUMMARY OF THE INVENTION

It is an object of this invention to provide peptides with antimicrobial activity. The antimicrobial peptides of the present invention contain from about five to about twenty-six amino acids joined in a linear array by peptide bonds.

An object of the present invention is a broad spectrum bactericidal peptide, termed CG 117-136 herein, which has the sequence RPGTLCTVAGWGRVSMRRGT (SEQ. ID NO:22). Further objects are additional bactericidal peptides, particularly effective for *P. aeruginosa* but not for *S. aureus* or *N. gonorrhoeae*, which peptides are termed CG 61-80 and CG 198-223, herein. CG 61-80 has the sequence RRENTQQHITARRAIRHPQY (SEQ ID NO:19) and CG 196-223 has the sequence GKSSGVPPEVFTRVSSFLPWIRTTMR (SEQ ID NO:26).

In other embodiments, the peptides comprise the amino acid sequences IIGGR (SEQ ID NO:1), IVGGR (SEQ ID NO:2), IIGGRESRPHSRPYMAYLQI (SEQ ID NO:16) and HPQYNR (SEQ ID NO:3). The peptide of the sequence IIGGRESRPHSRPYMAYLQI is particularly preferred. A consensus sequence for peptides related to HPQYNQR (SEQ ID NO:3) has been formulated: $HX_1X_2X_3X_4X_5X_6$, where $X_1$ is proline, histidine or alanine; $X_2$ is aspartic acid, asparagine, glutamic acid, glutamine, alanine, serine, threonine, isoleucine, valine, histidine, tyrosine, arginine, methionine oxide or methionine sulfone; $X_3$ is tyrosine, phenylalanine, tryptophan or beta-naphthyl-alanine; $X_4$ is asparagine or alanine; $X_5$ is glutamine, proline, N-methyl alanine, or alanine; and $X_6$ is arginine, lysine, alanine or NH_2 or OH (SEQ ID NO:4).

A peptide fitting the consensus sequence preferably has at position 3 (as $X_2$ above) a nonbulky, hydrophilic amino acid capable of hydrogen bonding, glutamine or proline at position 6 (as $X_5$ above) and lysine or arginine at position 7 (as $X_6$ above). Preferably amino acid 3 is glutamine, alanine, glutamate, asparagine, or aspartate. Antimicrobial peptide sequences whose sequences fall within the consensus sequence include, but are not limited to, HPQYNQR (SEQ ID NO:3), HPAYNPK (SEQ ID NO:5), HPAYNPR (SEQ ID NO:6) and HPAYNQR (SEQ ID NO:7). Additional antimicrobial peptide sequences related to HPQYNQR include, but are not limited to, HPQYAQR (SEQ ID NO:8), HPQYNQA (SEQ ID NO:9), HPQYNAR (SEQ ID NO:10), HPAYNPR (SEQ ID NO:6), HAQYNQR (SEQ ID NO:11), and HPQYNQ (SEQ ID NO:12) and RHPQYNQR (SEQ ID NO:13). These peptides possess microbicidal activity for Gram positive and Gram negative bacteria. The oligopeptide corresponding in sequence to amino acid 77-96 of mature cathepsin G, HPQYNQRTIQNDIMLLQLSR (SEQ ID NO:14), is not significantly bactericidal, however, for *P. aeruginosa*, *N. gonorrhoeae* or *S. aureus*.

An object of the present invention is to provide antimicrobial peptides which are useful as bactericides and/or bacteriostats, useful, for example, for inhibiting microbial growth in a variety of solutions and sterile solutions, such as contact lens solutions, herbicidal solutions, hazardous or refuse waste streams, surface disinfectant solutions and oil recovery fluids.

A further object of the invention is to provide therapeutic compositions, suitable for human, veterinary, agricultural or pharmaceutical use, comprising one or more of the antimicrobial peptides of the present invention and a suitable pharmacological carrier. Such therapeutic compositions can be formulated as understood in the art, e.g., for topical or aerosol application, for controlling and/or preventing infection by Gram positive or Gram negative bacteria or fungi. Preferably, the antimicrobial peptides of the present invention are used in the treatment of infections by Gram-negative or Gram-positive bacteria. The antimicrobial peptides of the present invention, when used in therapeutic compositions, will not have significant immunogenic activity. In vitro antimicrobial activity of the oligopeptides of the present invention is an accurate predictor of in vivo antimicrobial activity.

Pharmaceutical compositions contain a therapeutically effective amount of an antimicrobial peptide. A therapeutically effective amount of an antimicrobial peptide can be readily determined according to methods known in the art. Pharmaceutical compositions are formulated to contain the therapeutically effective amount of an antimicrobial peptide and a pharmaceutically acceptable carrier appropriate for the route of administration (topical, gingival, intravenous, aerosol, local injection) as known to the art. For agricultural use, the composition comprises a therapeutically effective amount of an antimicrobial peptide and an agriculturally acceptable carrier suitable for the organism (e.g., plant) to be treated. Preferably for use in a pharmaceutical composition, the antimicrobial peptide will have an $ED_{50}$ in vitro less than about $10^{-3}M$. The skilled artisan can readily determine a therapeutically effective amount against a target bacterial strain, for example, based on the $ED_{50}$ using the methods disclosed herein and the teachings of the art.

Therapeutic compositions may be administered by topical, dental rinse, aerosol or intravenous application, or by local injection for the control or prevention of infection or control of tumor cell growth, by any means known to the art.

The IIGGR-related antimicrobial oligopeptides, including IIGGR (SEQ ID NO:1), IVGGR (SEQ ID NO:2) and IIGGRESRPHSRPYMAYLQI (SEQ ID NO:16), of the present invention may also be used to kill or control the growth of tumor cells or virus-infected cells. In such applications, these peptides will be particularly useful when coupled to antibodies or other molecules which are specific for the target tumor cell or virus-infected cell so that the peptide acts specifically on the tumor or virus-infected cell.

BRIEF DESCRIPTION OF THE FIGURES

FIG. 2 shows Reverse Phase-HPLC fractionation of cathepsin G peptides obtained from clostripain fragmentation. Low $M_r$ peptides obtained by gel filtration chromatography were lyophilized, dissolved in 250 microliters of 0.1% (v/v) TFA and subjected to RP-HPLC as described in the Examples. Peptides were eluted in several peaks (1-10). These were further purified, separately, by RP-HPLC as described herein. Only peptides in peaks 6 and 7 were found to exert antibacterial action in vitro against *S. aureus* and *N. gonorrhoeae*.

FIG. 3 illustrates the bactericidal activity of synthetic peptides derived from cathepsin G. Synthetic peptides (0-100 µg) were tested against *N. gonorrhoeae* and *S. aureus* as described in the Examples. Each data point represents the mean of three determinations from three separate experiments using the same lot of synthetic peptide.

FIG. 8 illustrates the complete amino acid sequence (SEQ ID NO:41) for the mature human cathepsin G, as deduced from analysis of its cDNA. In the chymotrypsin nomenclature, it displays the charge relay profile of His57 Asp102 Ser195 that is typical of serine proteases; the charge relay system amino acids are identified with an asterisk (*). The Ser195 residue (residue 181 in the mature cathepsin G protein) is the target of phosphorylation by DFP, resulting in irreversible inhibition of chymotryptic activity. The residues lining the primary specificity pocket of cathepsin G are marked with #.

FIG. 9 presents hydrophobicity analysis for peptide CG 117-136 (SEQ ID NO:22) and the corresponding hydrophobicity-hydrophilicity plot for the amino acid sequence.

FIG. 10 presents a comparison of the amino acid sequence of the broad spectrum antibacterial peptide CG 117-136 (SEQ ID NO:22) with related sequences in other antibacterial proteins and serine proteases. The dots represent amino acid residue identity with the CG 117-136 sequence. The partial sequences of human granzyme B, mouse granzyme B, CAP 37, human elastase, proteinase 3 and bovine chymotrypsin correspond to SEQ ID NOs: 42, 44, 45, 46 and 47, respectively.

DETAILED DESCRIPTION OF THE INVENTION

Figure 1:
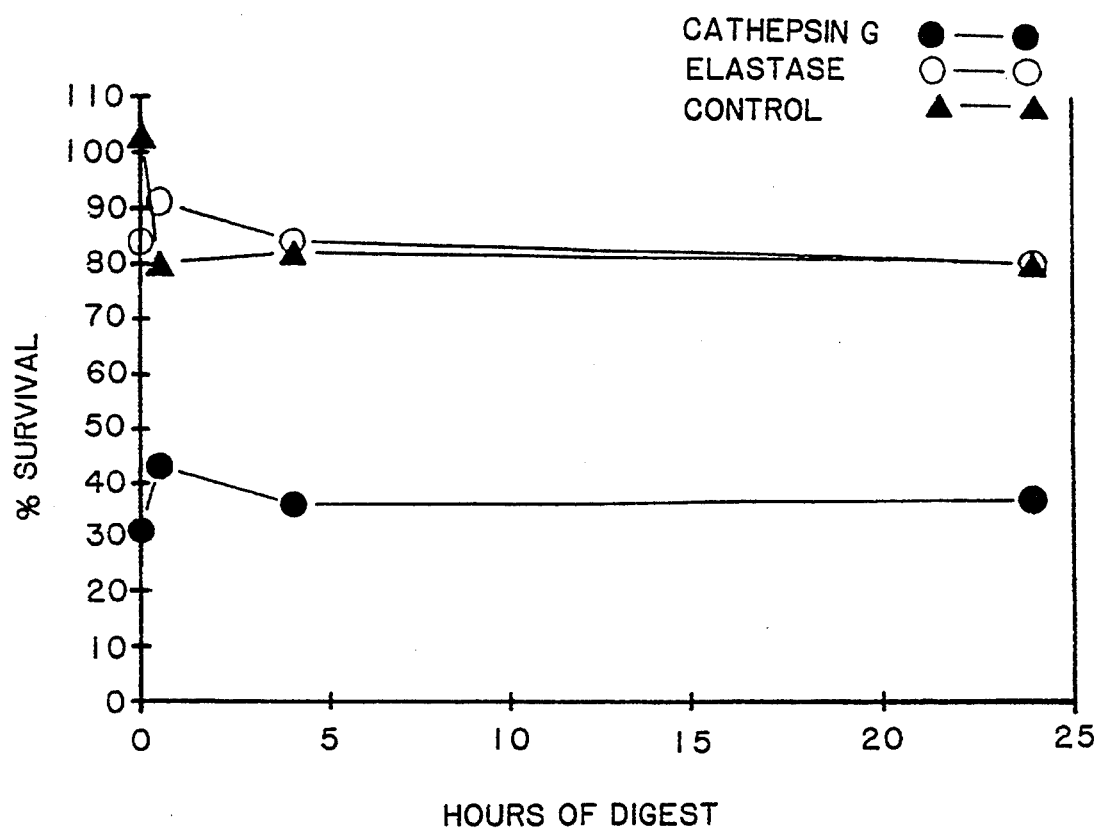
FIG. 1 illustrates the bactericidal activity of clostripain digests of human neutrophil cathepsin G and elastase. Proteinases were digested as described in the Examples, lyophilized, dissolved in HBSS (pH 7.5), and tested (50 µg/ml) for antibacterial activity against *S. aureus* strain 8325-4. Each data point represents the mean of three samples with <5% variance between each.

As used herein, an oligopeptide is composed of from about five to about twenty-seven amino acids linked together by peptide bonds in a linear array. The peptide may be in a linear conformation or it may assume secondary structure. A cyclic peptide derivative can also have antimicrobial activity, and thus is a functional equivalent of the antimicrobial peptides of the present invention. Sequences are conventionally given from the amino terminus to the carboxyl terminus. The peptides of the present invention have antimicrobial activity by themselves or when coupled to another molecule, e.g., polyethylene glycol or a carrier protein such as bovine serum albumin, so long as the peptides are positioned such that they can come into effective contact with the target cell.

Table 1 presents most abbreviations used in this application. Other abbreviations are as commonly used in the art.

TABLE 1

| Abbreviations | | | |
|---|---|---|---|
| A | = Ala = Alanine | M | = Met = Methionine |
| C | = Cys = Cysteine | N | = Asn = Asparagine |
| D | = Asp = Aspartic Acid | P | = Pro = Proline |
| E | = Glu = Glutamic Acid | Q | = Gln = Glutamine |
| F | = Phe = Phenylalanine | R | = Arg = Arginine |
| G | = Gly = Glycine | S | = Ser = Serine |
| H | = His = Histidine | T | = Thr = Threonine |
| I | = Ile = Isoleucine | V | = Val = Valine |
| K | = Lys = Lysine | W | = Try = Tryptophan |
| L | = Leu = Leucine | Y | = Tyr = Tyrosine |
| Boc | = tert-butyloxycarbonyl | | |
| CFU | = colony forming unit | | |
| DFP | = diisopropylfluorophosphate | | |
| HLE | = human leukocyte elastase | | |
| Pam | = (phenylacetamido) methyl | | |

$ED_{50}$ is the concentration of an antimicrobial agent which kills (or otherwise inhibits growth) 50% of the input indicator microorganism or cell under particular test conditions.

For convenience, the peptides newly disclosed herein are named according to the amino acid positions in mature Cat G (FIG. 8) CG 1-20 represents amino acid residues 1-20 of the mature Cat G sequence and has the sequence IIGGRESRPHSRPYMAYLQI (SEQ ID NO:16).

CG 21-40 corresponds in sequence to amino acids 21-40 of Cat G, QSPAGQSRCGGFLVREDFVL (SEQ ID NO:17).

CG 41-60, corresponding to amino acids 41-60 of Cat G, has the sequence TAAHCWGSNINVTLGAHNIQ (SEQ ID NO:18).

CG 61-80, corresponding to amino acids 61-80 of Cat G, has the sequence RRENTQQHITARRAIRHPQY (SEQ ID NO:19).

CG 77-96, corresponding to amino acids 77-96 of Cat G, has the amino acid sequence HPQYNQRTIQN-DIMLLQLSR (SEQ ID NO:20).

CG 97-116, corresponding to amino acids 97-116 of Cat G, has the sequence RVRRNRNVNPVAL-PRAQEGL (SEQ ID NO:21).

CG 117-136, corresponding to amino acids 117-136 of Cat G, has the sequence RPGTLCTVAGWGRVSMRRGT (SEQ ID NO:22).

CG 137-156, corresponding to amino acids 137-156 of Cat G, has the sequence DTLREVQLRVQRDRQCLRIF (SEQ ID NO:23).

CG 157-176, corresponding to amino acids 157-176 of Cat G, has the sequence GSYDPRRQICVGD-RRERKAA (SEQ ID NO:24).

CG 177-197, corresponding to amino acids 177-197 of Cat G, has the sequence FKGDSGGPLLCNNVAHGIVSY (SEQ ID NO:25).

CT 198-223, corresponding to amino acids 198-223 of Cat G, has the sequence GKSSGVPPEVFTRFVSSFLPWIRTTMR (SEQ ID NO:26).

Antimicrobial activity, as used herein, refers to the ability of a peptide of the present invention to kill at least one species selected from the group consisting of Gram positive bacteria, Gram negative bacteria, fungi, and protozoans. It is increasingly preferred that the peptide kill at least 50%, 60%, 70%, 80%, 90% or all cells of at lest one species of gram positive or gram negative bacteria, fungi, or protozoans. Sensitive Gram positive bacteria can include, but are not limited to, *Staphylococcus aureus*. Sensitive Gram negative bacteria include, but are not limited to, *Escherichia coli, Neisseria gonorrhoeae*, and *Pseudomonas aeruginosa*. Periodontal disease-associated bacteria include *Capnocytophaga sputigena, Actinobacillus actinomycetemcomitans* and *Eikenella corrodens. Capnocytophaga sputigena* ATCC 33123 is sensitive to IIGGR (SEQ ID NO:1), IIG- GRESRPHSRPYMAYLQI (SEQ ID NO:16) and HPQYNQ (SEQ ID NO:13). *A. acetinomycetemcomitans* is sensitive to IIGGR (SEQ ID NO:1) and HPQYNQR (SEQ ID NO:3). *E. corrodens* is more sensitive to IIGGR (SEQ ID NO:1) than to HPQYNQR (SEQ ID NO:3). Sensitive fungi can include, but are not limited to, *Candida albicans*. Antimicrobial activity can also refer to the ability to kill or inhibit the growth of other cells, in particular, those which are tumor cells or virus-infected cells.

The antimicrobial peptides of the present invention are oligopeptides which possess antimicrobial activity, as defined herein. These antimicrobial peptides may contain modifications such as acetylation, provided that the antimicrobial activity is not destroyed. Chemical modifications which do not destroy antimicrobial activity are those which do not substantially decrease the hydrophilicity of the antimicrobial peptide and those which are not bulky hydrophobic chemical groups, particularly for antimicrobial peptides related in sequence to HPQYNQR. Modified peptides with antimicrobial activity are functionally equivalent to the antimicrobial peptides of the present invention. Such modified peptides with antimicrobial activity include, but are not limited to, (1-methyl-H)QYNQR, (3-methyl-H)PQYNQR, (Ac—H)PQYNQR and HPAYNA$^M$K.

Antibacterial pharmaceutical compositions, as defined herein, comprise a pharmaceutically acceptable carrier and one or more antibacterial peptides of the present invention. Such antimicrobial pharmaceutical compositions may be formulated in ways, as understood in the art, for use for topical application, for gingival application (for gingivitis or periodontal disease) or for local or systemic injection. For use in the treatment or prevention of gingivitis, the peptides of the present invention can be incorporated in effective amounts in a dental rinse for application to the buccal area, or they may be incorporated in other suitable compositions for topical application. The antibacterial peptides of the present invention may also be incorporated in effective amounts in chewing gum, lozenges for sucking, toothpowder or toothpaste. The antibacterial peptides of the present invention can comprise from 0.001% to 50% by weight of such compositions. It will be understood that a composition for systemic injection will contain an antimicrobial peptide, e.g., an antibacterial peptide such as HPQYNQR, in a therapeutically effective amount or a therapeutically effective amount of an antimicrobial peptide can be conjugated to an antibody, or any other compound as understood in the art, with specificity for the target cell type. The choice of the peptide will be made with consideration of immunogenicity and toxicity to the infected host, effective dose of the peptide, and the sensitivity of the target microbe to the peptide, as well-understood in the art.

The Cat G protein was analyzed to determine whether the same portions of the protein were responsible for the enzymatic and antibacterial activity. Human Cat G was purified and digested with the proteolytic enzyme clostripain. Peptides resulting from that digestion were purified and individually tested for antibacterial and enzymatic activity. None of the peptides tested exhibited the chymotrypsin-like activity of the intact molecule. However, two Cat G-derived peptides exhibited antibacterial activity using *Staphylococcus aureus* or *Neisseria gonorrhoeae* as the indicator organism. Those peptides were IIGGR (SEQ ID NO:1) (peptide 1; amino acids 1-5) and HPQYNQR (peptide 2; amino acids 77-83) (SEQ ID NO:3). Similar antibacterial activities were observed for synthetic peptides identical in sequence to the above-noted peptides. Similarly, the oligopeptide corresponding in amino acid sequence to amino acids 1-20 of Cat G (i.e., SEQ ID NO:16) exhibited strong bactericidal activity against *Pseudomonas aeruqinosa*. Even more effective as an antimicrobial agent is the oligopeptide corresponding in sequence to amino acids 1-20 of Cat G, but which retains some blocking groups from the component derivatized amino acids in chemical peptide synthesis or an artifactual reaction product. The chemical identity of the substituents on that oligopeptide or reaction product have not yet been identified. FIG. 4(A) illustrates killing of *S. aureus*. and *N. gonorrhoeae* by these two peptides.

Figure 3A:
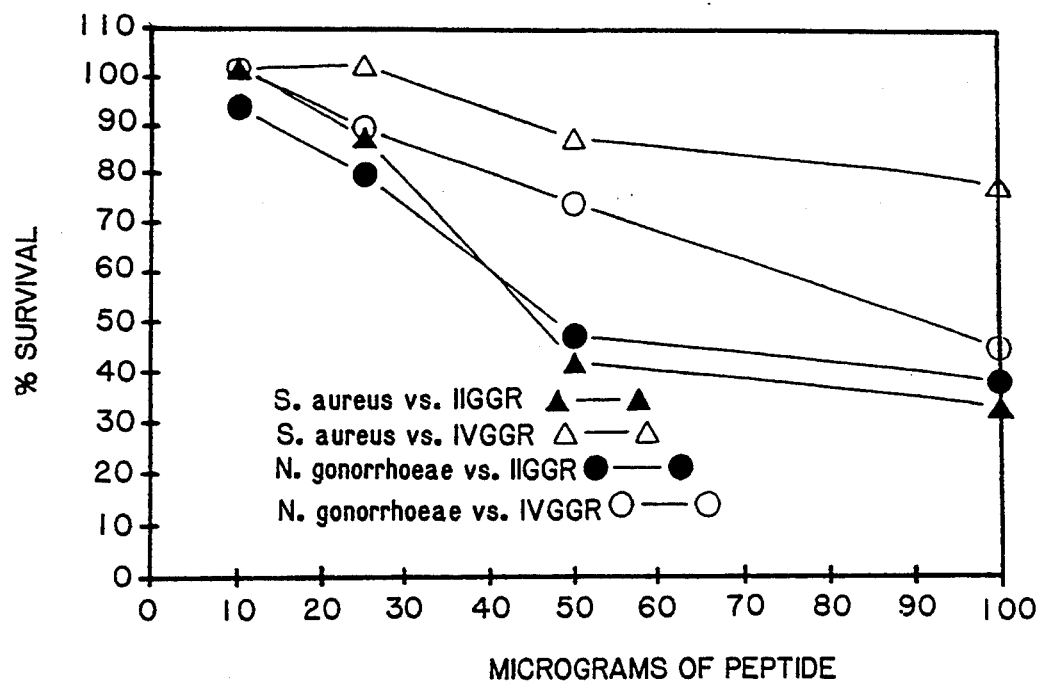
FIG. 3(A), peptides IIGGR (SEQ ID NO:1) vs. IVGGR (SEQ ID NO:2)

A peptide with a one amino acid substitution (V for I at position 2 of IIGGR (SEQ ID NO:1)) was synthesized and tested for antibacterial activity. This sequence is identical with the first five amino acids of human leukocyte elastase, CAP37 and azurocidin. Killing of both the Gram positive and the Gram negative test organism was less efficient with the IVGGR (SEQ ID NO:2) sequence ($ED_{50} > 8.75 \times 10^{-4}$M) than with the IIGGR sequence ($ED_{50} = 4.3 \times 10^{-4}$M), although the IVGGR sequence was somewhat more effective against gonococci than staphylococci (see FIG. 3A).

Figure 3B:
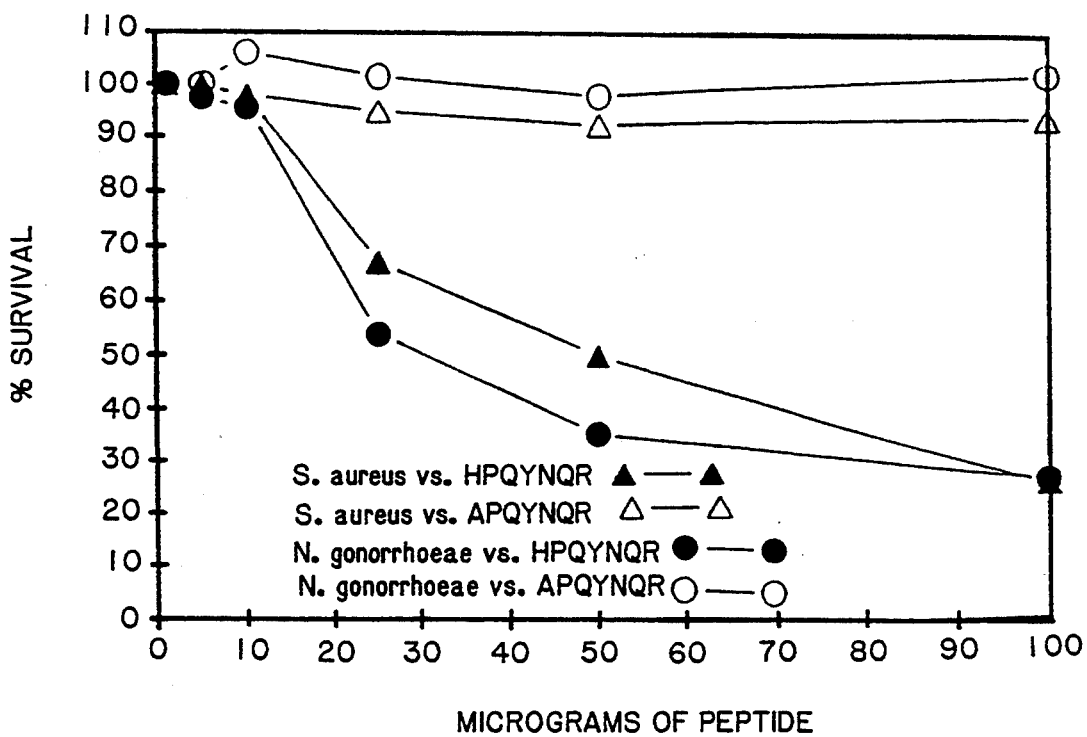
FIG. 3(B), peptides HPQYNQR (SEQ ID NO:3) vs. APQYNQR (SEQ ID NO:15).

Killing of staphylococci and gonococci by HPQYNQR (SEQ ID NO:3) and APQYNQR (SEQ ID NO:27) was also tested. The results are shown in FIG. 3(B); for HPQYNQR (SEQ ID NO:3) the $ED_{50} = 1.19 \times 10^{-4}$M for *S. aureus*, and the $ED_{50}$ for *N. gonorrhoeae* was $5.0 \times 10^{-5}$M. The replacement of histidine with alanine (APQYNQR) abolished its bactericidal activity for both microorganisms.

Figure 4:
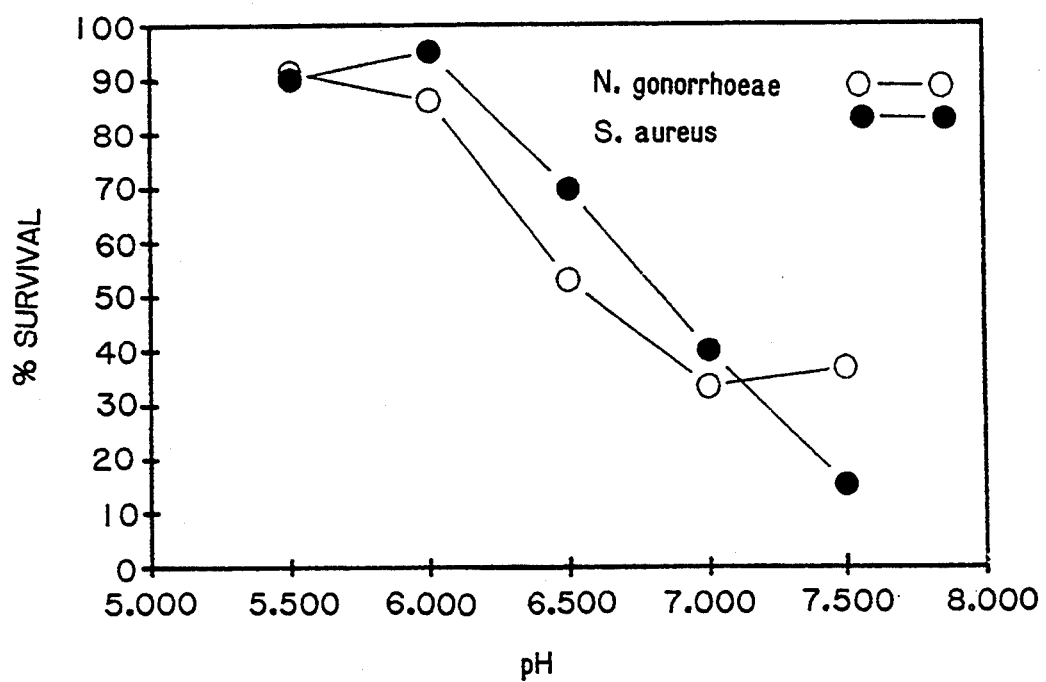
FIG. 4 illustrates the pH dependency for the bactericidal activity of HPQYNQR (SEQ ID NO:3). Aliquots of peptide (100 µg) were assayed for antibacterial activity in incubation with either of the two test bacteria at different pH values, as described herein. Each data point is the average of two determinations from three separate experiments.
Figure 6A:
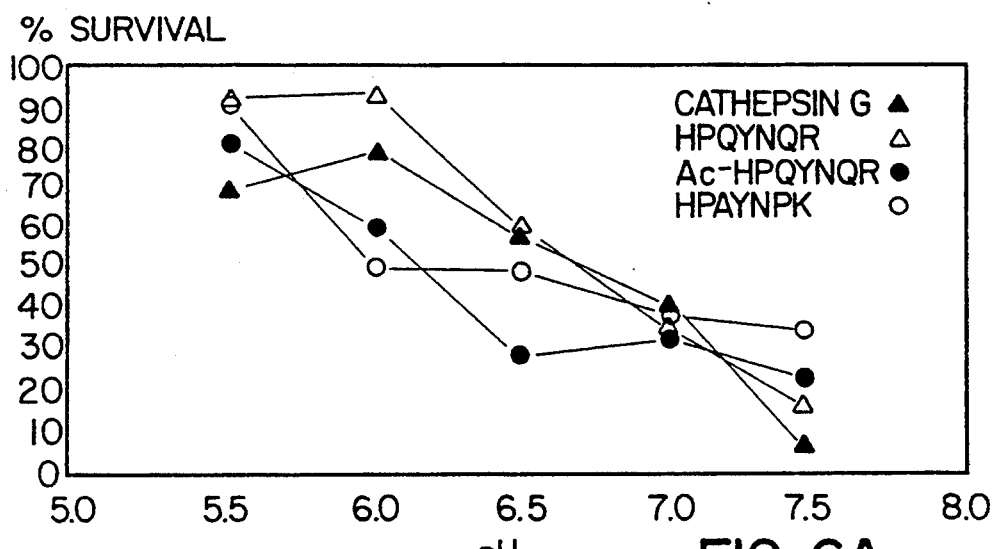
FIG. 6 illustrates the bactericidal action of Cat G synthetic peptides (HPQYNQR, Ac-HPQYNQR (SEQ ID NO:3)) (see Table 2), and human granzyme B-derived peptide (HPAYNPK (SEQ ID NO:5)) under conditions of different pH, FIG. 6A and ionic strength, FIG. 6B, and at different time points FIG. 6C. The synthetic peptides ($5 \times 10^{-4}M$) and purified, enzymatically inactive Cat G ($1.8 \times 10^{-6}M$), were tested against *S. aureus* in HBSS modified to different pH FIG. 6A and ionic strengths FIG. 6B. Standard ionic strength HBSS was used in FIG. 6A, while pH 7.5 HBSS was used in FIG. 6B. The peptides and Cat G preparations are identified in the inserts. The results are mean values from three separate experiments.
FIG. 6C Time course of killing *S. aureus* by Cat G and granzyme B-derived synthetic peptides. Synthetic peptides (5×10⁻⁴M) were tested for bactericidal action over a 120 min period in optimal HBSS. The results are from three separate experiments and mean values.
Figure 6B:
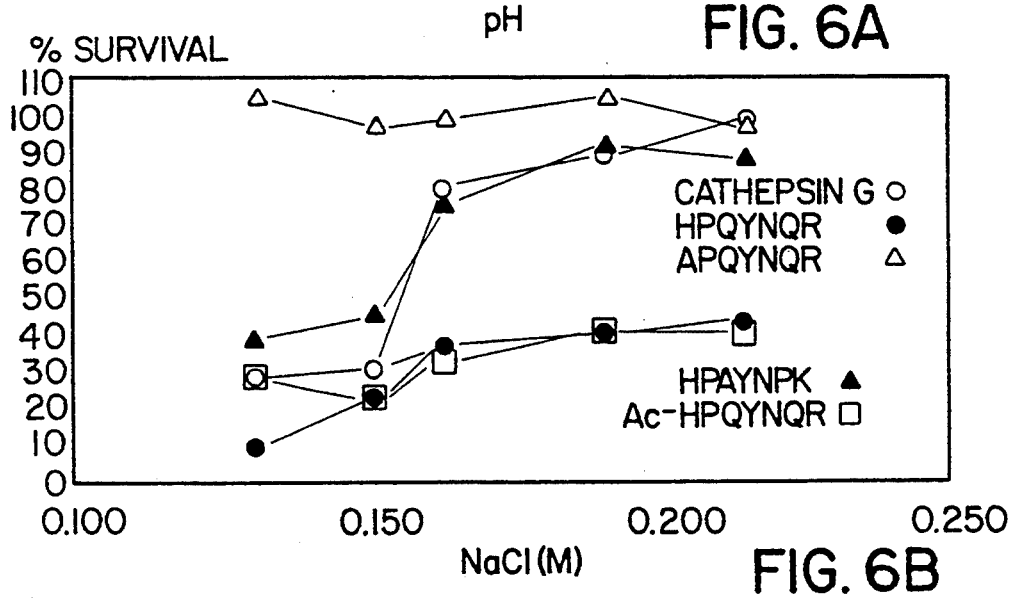

Antimicrobial activity of the Cat G-derived peptides was found to be dependent on assay temperature, pH and ionic strength. As for full-length Cat G, effective killing of *S. aureus* by the synthetic peptides was optimal at 37° C. with activity from about 30° to about 39° C., and was optimal at pH values of 7.0-7.5 for the range of pH values tested (Results for HPQYNQR (SEQ ID NO:3) are shown in FIGS. 4 and 6B). The antimicrobial action of these peptides was optimal in standard HBSS (0.12M NaCl); conditions of increased ionic strength (0.17-0.21M NaCl) completely inhibited the antibacterial action (FIG. 6B) except for peptides HPQYNPK (SEQ ID NO:49) or Ac-HPQYNQR.

Because the peptides tested individually showed significantly less activity than the natural Cat G protein or the clostripain digest, IIGGR (SEQ ID NO:1) and HPQYNQR (SEQ ID NO:3) were tested for synergistic activity. Under optimal conditions of temperature, pH and ionic strength, IIGGR and HPQYNQR together were about twice as active against *S. aureus* than when tested individually, but still less active than native Cat G or a clostripain digest of Cat G. A synthetic peptide consisting of the peptides 1 and 2 joined by a bridge (AIR) had activity similar to that of HPQYNQR alone ($ED_{50} = 5.0 \times 10^{-5}$M). Thus, these two peptides together were less effective against *S. aureus* than natural Cat G ($ED_{50} = 4.0 \times 10^{-6}$M), suggesting that other antimicrobial domains or sequences flanking peptides 1 and 2 in the full-length molecule contribute to the total antimicrobial activity of full-length Cat G. Alternatively, other peptides in the clostripain-Cat G digestion mixture may have potentiated the activity of IIGGR (SEQ ID NO:1) and HPQYNQR (SEQ ID NO:3).

Figure 5:
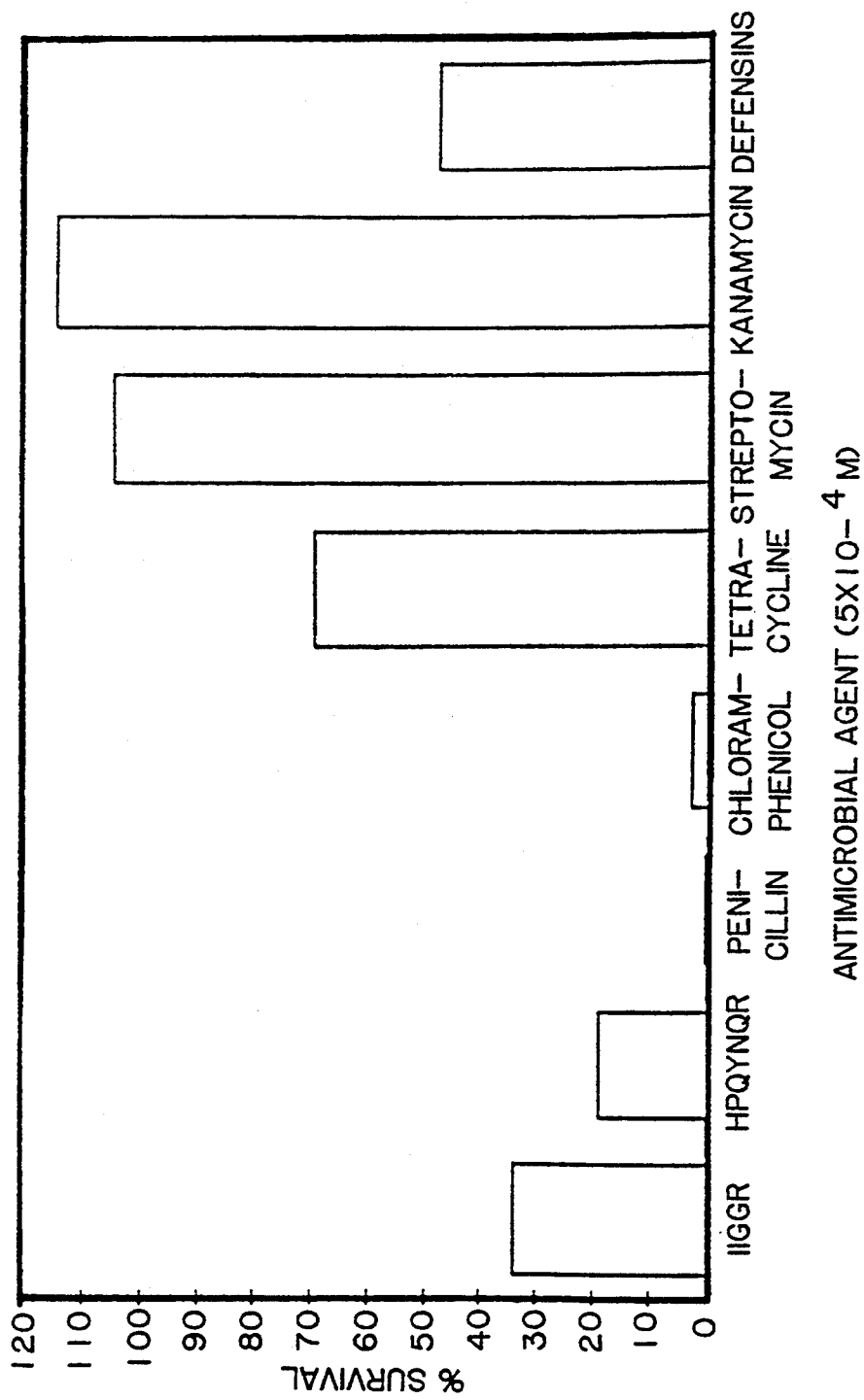
FIG. 5 compares the bactericidal capacities of Cat G synthetic peptides and certain antibiotics. *N. gonorrhoeae* strain FA 102 was exposed to $5.0 \times 10^{-4}M$ of IIGGR (SEQ ID NO:1), HPQYNQR (SEQ ID NO:3), penicillin G, chloramphenicol, tetracycline, streptomycin, kanamycin, and a mixture of three partially purified human defensins in HBSS (pH 7.5). After 30 min at 37° C. the samples were plated onto GCB agar, incubated for 48 hr, and colonies counted. There were no gonococcal colonies after 48 hr of incubation.

The antibacterial activities of IIGGR (SEQ ID NO:1) and HPQYNQR (SEQ ID NO:3) were compared with other known antimicrobial agents (FIG. 5). These peptides exhibited activities roughly comparable to those of a pool of defensins and to the clinically useful antibiotics chloramphenicol and tetracycline (test concentration of each compound $5.0 \times 10^{-4}$M). For the heptapeptides, this corresponds to about 100 micrograms per ml. Chloramphenicol was more effective at this concentration than the defensin pool or the test peptides, and these peptides from Cat G were more active than tetracycline, streptomycin, kanamycin or the defensin pool.

IIGGR (SEQ ID NO:1) and HPQYNQR (SEQ ID NO:3) were used to search known protein sequences of other cytotoxic serine proteases present in the cytolytic lymphocytes of mice and humans for partial amino acid sequence identities. Proteins containing the IIGGR sequence at the N-termini include Cat G and eosinophil cationic protein (Gleich et al. (1986) Proc. Natl. Acad. Sci. USA 83:3146-3150). Human leukocyte elastase (Gabay et al. (1989) supra; azurocidin (Sinha et al. (1987) Proc. Natl. Acad. Sci. USA 84:2228-2232); and CAP 37 (Pereira et al. (1990) J. Clin. Invest. 85:1468-1476) begin with the sequence IVGGR (SEQ ID NO:2). Human leukocyte elastase does not have antimicrobial activity in vitro. CCCP I and human lymphocyte granzymes B, D, E and G begin with IIGGH (SEQ ID NO:28) while RMCP II begins with the sequence IIGGV (SEQ ID NO:29) (Salvesen et al. (1987) supra). It may be assumed that the IIGGR (SEQ ID NO:1) of Cat G is located on the interior of the protein because it forms a salt bridge with Asp-170, a residue which has been invariably identified to be a part of the binding site of other chymotrypsin-like serine proteases. This Cat G residue corresponds to Asp-102 in the catalytic triad of chymotrypsin. This hypothesis is consistent with the X-ray crystallographic structure of chymase (Remington et al. (1988) Biochemistry 27:8097-8115), which has significant sequence similarity with Cat G; a similar domain is buried in the interior of the molecule. It is probable that HPQYNQR is oriented toward the surface of Cat G because of the positioning of an analogous sequence in chymase, the structure of which has been predicted.

Human granzymes A and B (granzyme B is also known as human lymphocyte protease) both contain internal sequences related to HPQYNQR (SEQ ID NO:3). HPAYNPK (SEQ ID NO:5), corresponding to an internal region of human leukocyte protease, possesses broad spectrum antimicrobial activity in vitro. The related sequences of mouse granzymes A, C, E, F and G do not possess such activity (see Table 5).

Variant peptides related to the sequences IIGGR and HPQYNQR were tested for antimicrobial activity. The results of testing variant sequences of the HPQYNQR peptide sequence for antimicrobial activity has led to the formulation of a consensus sequence for an antimicrobial peptide: $HX_1X_2X_3X_4X_5X_6$ (SEQ ID NO:4).

Preferably $X_1$ is proline, alanine or histidine; $X_2$ is one of asparagine, aspartic acid, glutamine, glutamic acid or alanine; $X_3$ is tyrosine or phenylalanine; $X_4$ is asparagine or alanine; $X_5$ is proline, glutamine, alanine or N-methyl alanine; and $X_6$ is lysine, arginine, alanine, —OH or —NH$_2$.

Antimicrobial hexa- and heptapeptide sequences falling within the consensus sequence include, but are not limited to, HPQYNQR (SEQ ID NO:3), HPAYNPK (SEQ ID NO:5), HPAYNPR (SEQ ID NO:6) and HPQYNQR (SEQ ID NO:3). Additional antimicrobial peptide sequences related to HPQYNQR include, but are not limited to, HPQYAQR (SEQ ID NO:8), HPQYNQA (SEQ ID NO:9), HPQYNAR (SEQ ID NO:10), HPQYNPR (SEQ ID NO:30), HAQYNQR (SEQ ID NO:11), HPQYNQ (SEQ ID NO:12), HHQYNQR (SEQ ID NO:31) and HPQYNQ$^M$K. Preferably, the oligopeptides consist essentially of the foregoing sequences. CG 77-96 (HPQYNQRTIQN-DIMLLQLSR) (SEQ ID NO:14) does not exhibit antimicrobial activity.

To determine the amino acids essential for the broad spectrum activity of HPQYNQR (SEQ ID NO:3), synthetic peptides with single alanine substitutions were prepared and tested for their antibacterial activity in vitro. The parental peptide sequence HPQYNQR and the following alanine-substituted derivatives (HPAYNQR (SEQ ID NO:7), HPQYAQR (SEQ ID NO:8) and HPQYNQA) (SEQ ID NO:9) exerted antibacterial action in vitro against S. aureus strain 8325-4 at a concentration of about $5 \times 10^{-4}$M, while certain other alanine-substituted derivatives (HPQYNAR (SEQ ID NO:10) and HPAYNPR) (SEQ ID NO:6) had reduced antibacterial activity, and still others (APQYNQR (SEQ ID NO:27) and HPQANQR (SEQ ID NO:32)) had no antibacterial activity in this assay. Similar activities or lack of activity was also observed with E. coli and with N. gonorrhoeae. These results are given in Table 2.

TABLE 2

Bactericidal Action of Synthetic Peptide Variants of Antimicrobial HPQYNQR

| Peptide Secquence[1] | % Survival of S. aureus | N |
|---|---|---|
| HPQYNQR (SEQ ID NO: 3) | 28.6 ± 1.57 | 15 |
| APQYNQR (SEQ ID NO: 27) | 98.5 ± 2.1 | 12 |
| HAPYNQR (SEQ ID NO: 11) | 31.2 ± 2.4 | 9 |
| HPAYNQR (SEQ ID NO: 7) | 43.6 ± 2.54 | 6 |
| HPQANQR (SEQ ID NO: 32) | 96.7 ± 4.34 | 6 |
| HPQYAQR (SEQ ID NO: 8) | 30.6 ± 0.85 | 6 |
| HPQYNAR (SEQ ID NO: 10) | 51.2 ± 3.6 | 6 |
| HPQYNQA (SEQ ID NO: 9) | 39.8 ± 1.96 | 6 |
| HPQKNTY (SEQ ID NO: 33) | 98.6 ± 2.13 | 3 |

[1]Antimicrobial synthetic peptide HPQYNOR, its derivatives with single alanine substitutions at each position, and a control peptide (HPQKNTY) were synthesized on an Applied Biosystem Model 403A peptide synthesizer (0.1 mmol scale) using phenylacetamidomethyl or p-methylbenzhydrylamine copoly (styrene/divinyl benzene) resins (Applied Biosystems, Inc.) and tert-butyloxycarbonyl (Boc)-protected amino acids. The data are presented as % survival ± SEM and represent results from at least 3 separate experiments for each peptide with S. aureus as the indicator organism.

These results suggest that the N-terminal histidine and the tyrosine residue at position 4 may be important determinants for the antibacterial activity of HPQYNQR (SEQ ID NO:3). To more closely examine the structural requirements of this peptide sequence needed for microbicidal activity, several additional peptides (see Table 4) containing alterations in either His-1 or Tyr-4 and a truncated peptide lacking Arg-7 were prepared and tested for killing of the S. aureus indicator organism. Methylation of nitrogen at position 1 or 3 of the imidazole ring of His-1 had little effect on the antibacterial activity, but derivatives with the imidazole modified at nitrogen-3 with more bulky benzyl or dinitrophenyl groups were inactive. Moreover, a synthetic peptide containing the D-stereoisomer of His was also inactive. Thus it appears that major modifications of the imidazole ring of His-1 abolish antibacterial activity, perhaps due to impaired hydrogen bonding with other amino acid side chains. While replacement of Tyr-4 by alanine inhibited antibacterial activity (Table 2), partial activity was observed where phenylalanine was present as the fourth residue, suggesting that an aromatic amino acid at position 4 is critical to antibacterial activity. The truncated pentapeptide HPQYN-amide was inactive, while the hexapeptide HPQYNQ-amide had antibacterial activity, suggesting that at least six amino acid residues are necessary to form a structure effective for antimicrobial activity. (See Table 3.) Surprisingly, an oligopeptide of the sequence HPQYNQ-RTIQNDIMLLQLSR (SEQ ID NO:14) did not exhibit significant antimicrobial activity against either *S. aureus* or *P. aeruginosa*.

TABLE 3

Bactericidal Action of Synthetic Derivatives of Antimicrobial Peptide HPQYNQR

| Peptide Sequence[1] | % Survival of *S. aureus* | N |
|---|---|---|
| HPQYNQR (SEQ ID NO: 3) | 28.6 ± 1.57 | 15 |
| APQYNQR (SEQ ID NO: 27) | 98.5 ± 2.1 | 12 |
| H$^{1m}$QYNQR | 37.3 ± 2.25 | 3 |
| H$^{3m}$PQYNQR[2] | 18.3 ± 3.82 | 3 |
| H$^{Dnp}$PQYNQR[2] | 102.2 ± 2.92 | 8 |
| H$^{Benzyl}$PQYNQR[2] | 99.0 ± 2.6 | 6 |
| $^{Ac}$HPQYNQR | 31.0 ± 1.6 | 5 |
| $^{Hep}$HPQYNQR | 97.0 ± 2.8 | 3 |
| D-HPQYNQR | 98.6 ± 1.6 | 5 |
| HPAYNQR (SEQ ID NO: 7) | 43.6 ± 2.54 | 6 |
| HPQANQR (SEQ ID NO: 32) | 96.7 ± 4.34 | 6 |
| HPQFNQR (SEQ ID NO: 34) | 45.0 ± 4.91 | 6 |
| HPQYNQA (SEQ ID NO: 9) | 39.8 ± 1.96 | 6 |
| HPQYNQ-amide | 32.8 ± 1.83 | 3 |
| HPQYN-amide | 98.5 ± 2.85 | 5 |

[1]All peptides were tested at 5 × 10$^{-4}$M as described in Table 2.
[2]Modified histidines are 1-methyl (1m), 3-methyl (3m), 2,4-dinitrophenyl (Dnp), benzyl, acetyl (Ac), and heptanoyl (Hep), and D stereoisomer (D-HPQYNQR) as described in the text.

To learn whether the hydrophilic nature of HPQYNQR is an important feature for antibacterial action, derivatives containing an acetyl or an heptanoyl moiety attached to the N-terminal amino group were synthesized and tested. The small increase in hydrophobicity imparted by the acetyl group has no significant effect, while the more bulky and hydrophobic heptanoyl group rendered the HPQYNQR (SEQ ID NO:3) derivative inactive.

Peptides corresponding or related to sequences within mouse granzymes A, B, C, D, E, F and G and human granzymes A and B were synthesized. As shown in Table 4, only the synthetic peptides corresponding to mouse granzyme B and human granzyme B had some antibacterial activity.

The human granzyme B-derived peptide differs from the Cat G peptide at positions 3, 6 and 7. To test how these differences affected antibacterial activity, variants of the Cat G and granzyme B peptides containing some of these heterologous amino acids or with alanine substitution at position 3 or 6 were synthesized and tested (Table 5). Placement of the Ala-3 residue in the Cat G only had a slight effect on antibacterial action (Tables 2 and 4). Conversely, placement of the Gln-3 residue in the Granzyme B peptide severely inhibited antibacterial activity. The Pro-6 residue of the granzyme B peptide also appeared to be crucial, because the replacement of Pro-6 with alanine abolished microbicidal activity. To further test the importance of Pro-6, a derivative containing N-methylalanine, which lacks the ring structure of proline but might mimic its hydrogen bonding potential, was synthesized and found to have antibacterial activity. The contribution of the Pro-6 residue to antibacterial activity in the granzyme B-derived peptide appeared to be unique for this peptide, because substitution at position 6 in the Cat G-derived peptide suppressed antibacterial activity. Further derivatives of HPQYNQR (SEQ ID NO:3) with amino acid replacements at the third position were synthesized and tested for antimicrobial activity. HPNYNQR (SEQ ID NO:35) and HPEYNQR (SEQ ID NO:36) had antimicrobial activity comparable to that of HPAYNQR (SEQ ID NO:37) while HPLYNQR (SEQ ID NO:37) lacked activity in the assay. (Table 4) HPDYNQR (SEQ ID NO:53) will have activity comparable to that of HPAYNQR (SEQ ID NO:7).

TABLE 4

Activity of Cat G Peptides with Third Position Replacements

| Peptide | Percent Survival |
|---|---|
| HPQYNQR (SEQ ID NO: 3) | 21.2% |
| HPAYNQR (SEQ ID NO: 7) | 40.3% |
| HPEYNQR (SEQ ID NO: 36) | 45.3% |
| HPNYNQR (SEQ ID NO: 35) | 42.9% |
| HPLYNQR (SEQ ID NO: 37) | 100.8% |

TABLE 5

Bactericidal Action of Synthetic Human and Mouse Granzyme Peptides[1]

| Peptide | Sequence | % Survival of *S. aureus* | N |
|---|---|---|---|
| Cat G | HPQYNQR (SEQ ID NO: 3) | 28.6 ± 1.57 | 15 |
| Cat G (Pro-6) | HPQYNPR (SEQ ID NO: 50) | 78.7 ± 2.8 | 4 |
| Human granzyme A | YPCYDPA (SEQ ID NO: 51) | 102 ± 2.6 | 3 |
| Human granzyme B | HPAYNPK (SEQ ID NO: 5) | 36 ± 2.5 | 9 |
| Human granzyme B'[2] | HPAYNAK (SEQ ID NO: 52) | 97 ± 1.8 | 3 |
| Human granzyme B" | HPQYNPK (SEQ ID NO: 53) | 95.1 ± 3.4 | 5 |
| Human granzyme B''' | HPAYNPR (SEQ ID NO: 6) | 87.5 ± 4.3 | 5 |
| Human granzyme B'''' | HPAYNA$^m$K[3] | 40.5 ± 1.6 | 3 |
| Human granzyme B''''' | HPAYNP-amide | 42.5 ± 3.6 | 5 |
| Mouse granzyme A | YPCYDEY (SEQ ID NO: 54) | 99.5 ± 1.7 | 3 |
| Mouse granzyme B | HPDYNPK (SEQ ID NO: 55) | 62 ± 3.4 | 3 |
| Mouse granzyme C | HPDYNPD (SEQ ID NO: 56) | 104 ± 3.8 | 3 |
| Mouse granzyme D,E[2] | HPDYNAT (SEQ ID NO: 57) | 98 ± 2.7 | 3 |
| Mouse granzyme F | HPAYDDK (SEQ ID NO: 58) | 98 ± 1.9 | 3 |
| Mouse granzyme G | HPAFDRK (SEQ ID NO: 59) | 102 ± 2.8 | 3 |

[1]All peptides were tested at 5 × 10$^4$M as described in Table 2.
[2]Peptide sequences for mouse granzymes D and E are identical. Human granzyme B variants are designated B'-B'''''.
[3]A$^M$, N-methyl alanine.

While the deletion of the C-terminal lysine-7 residue from HPAYNPK (SEQ ID NO:5) had no effect on the bactericidal action of the granzyme B-related peptide, its replacement with arginine as in the Cat G peptide severely inhibited antibacterial activity.

As for the full-length Cat G, the antibacterial action of the granzyme B-derived peptide was found to be optimal at slightly basic pH (FIG. 6A) although, like the acetylated derivative of HPQYNQR, significant antibacterial activity was observed at a pH of 6.0. As for full-length Cat G, the antibacterial action of human granzyme B was also sensitive to increasing concentrations of NaCl in the incubation mixture. Surprisingly, the Cat G-derived peptide HPQYNQR (SEQ ID NO:3)

and its acetylated derivative retained antibacterial activity even at the highest NaCl concentration (0.21M) tested (FIG. 6B).

Figure 6C:
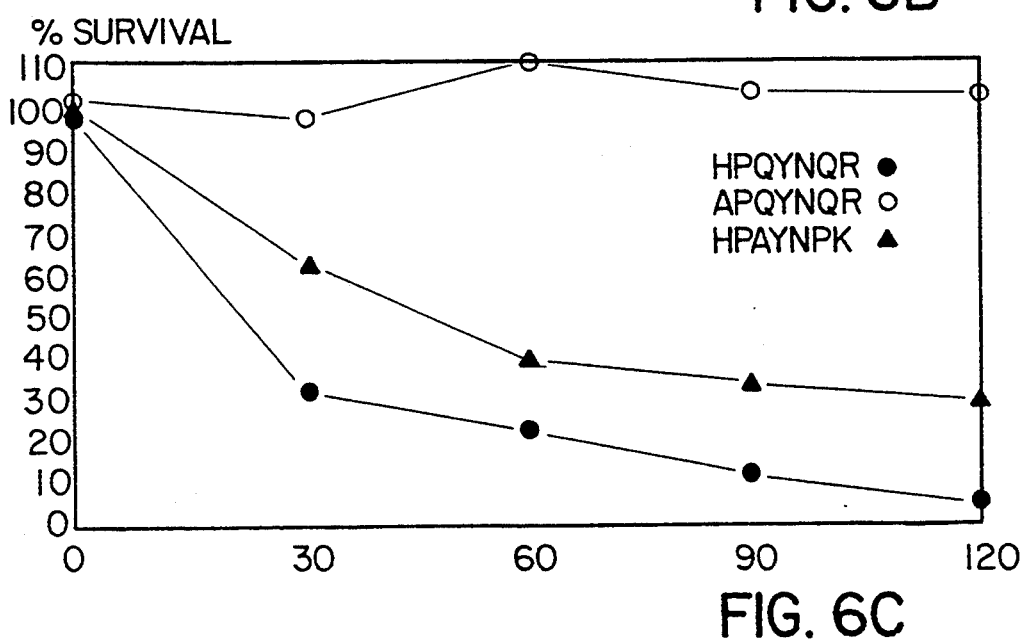

As seen with the Cat G-derived peptide, the antibacterial action of human granzyme B extended to *E. coli* and *N. gonorrhoeae* as well as *S. aureus*. Killing of the *S. aureus* indicator was more rapid with the Cat G-derived peptide than with the human granzyme B-derived peptide (FIG. 6C).

Results with variant peptides related to HPQYNQR (SEQ ID NO:3) suggest that the N-terminal histidine and the internal tyrosine residues were important in generating antimicrobial activity. A substitution of alanine for histidine, D-histidine for the L-isomer or the attachment of a 2,4-dinitrophenyl group to the imidazole group of L-histidine resulted in a loss of activity. Similarly, a substitution of alanine for tyrosine at position 4 led to a loss of microbicidal activity (see Table 4).

To determine whether hydrophilicity of the antimicrobial peptide was determinant of activity, HPQYNQR (SEQ ID NO:3) was modified by the addition of an acetyl or a heptanoyl group to the N-terminal amino group. Acetylation did not affect activity, while the heptanoyl derivative lacked antimicrobial activity.

The antibacterial activity of the HLP-derived peptide (HPAYNPK (SEQ ID NO:5)) cannot be readily explained using the Cat G sequence (HPQYNQR (SEQ ID NO:3)) as a canonical model. The alanine residue at position 3 and the proline at position 6 of the HLP-derived peptide cannot result from conservative amino acid changes in HPQNQR, although the lysine for arginine at position 7 is a conservative change. The ability of a position 7 substitution variant (alanine for arginine) of the Cat G sequence to retain significant killing activity might suggest that this is not a key position in determining activity. An alanine substitution at position 3 (for glutamine) decreased activity of the Cat G-related peptide.

The result of testing variant sequences of the HPQYNQR peptide sequence for antimicrobial activity has led to the formulation of a consensus sequence for an antimicrobial peptide. $HX_1X_2X_4X_5X_6$, where $X_1$ is proline, histidine or alanine; $X_2$ is aspartic acid, asparagine, glutamic acid, glutamine, alanine, serine, threonine, isoleucine, valine, histidine, tyrosine, arginine, methionine oxide or methionine sulfone; $X_3$ is tyrosine, phenylalanine, tryptophan or naphthyl-alanine; $X_4$ is asparagine or alanine; $X_5$ is glutamine, proline, alanine, or N-methyl alanine; and $X_6$ is arginine, lysine, alanine, —OH or —NH$_2$ (SEQ ID NO:4).

Figure 7:
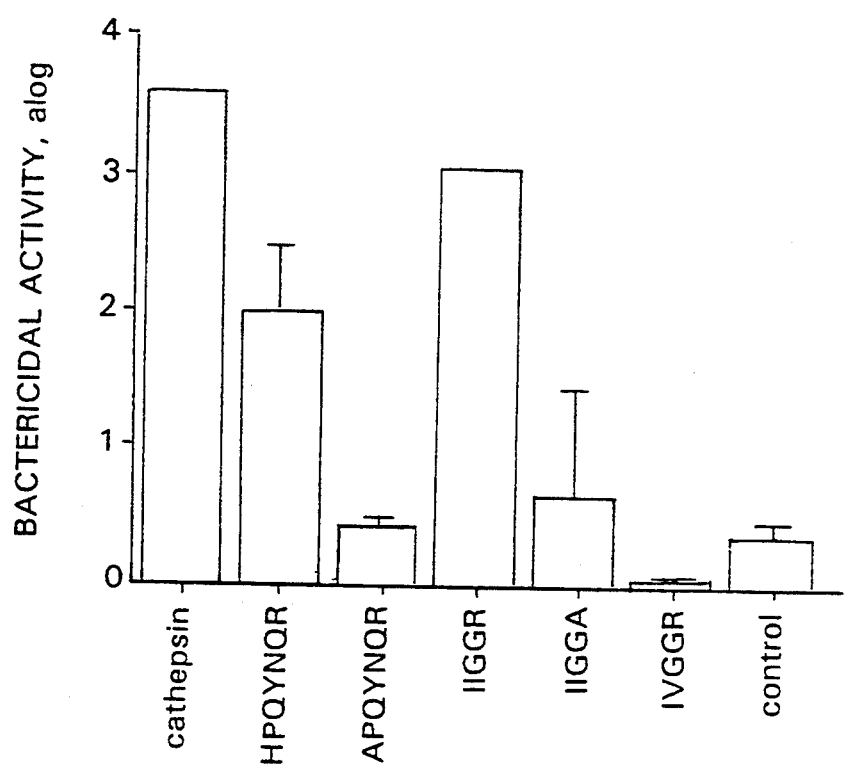
FIG. 7 graphically illustrates the in vitro bactericidal activity of various Cat G-related oligopeptides against *C. sputigena* ATCC 33123. $10^8$ cells/ml were incubated 2 h in 1/100 strength HBSS at a concentration of 100 µg/ml for cathepsin G, or at 500 µg/ml for peptides derived from cathepsin G. The y-axis gives bactericidal activity, as measured by logs (base 10) of lost viability.

Cat G-derived peptides were tested for antimicrobial activity against *Capnocytophaga sputigena* ATCC 33123, which is the same as that now available as *C. sputigena* ATCC 33612 (American Type Culture Collection, Rockville, Md.). *C. sputigena* is representative of oral pathogens associated with periodontal disease and/or gingivitis. As shown in FIG. 7, IIGGR (SEQ ID NO:1) and CG 1-20 (SEQ ID NO:16) are effective against *C. sputigena* ATCC 33123 in vitro. When incorporated in pharmaceutical compositions, one or more of the peptides related in sequence to Cat G can be used to ameliorate gingivitis and/or treat periodontal disease. Compositions for oral use include oral rinses, lozenges and formulations for topical application to the gums. The skilled artisan can use the teachings of the present specification and knowledge readily accessible to the art to prepare pharmaceutically useful formulations for oral application, topical or other applications, particularly after animal studies to confirm that these peptides are not toxic to the human or animal host and are effective in vivo.

Because the antimicrobial activity resulting from the IIGGR and HPQYNQR peptides recovered after clostripain digestion was less than 1% of the activity of intact Cat G, an alternate approach was pursued. Eleven peptides that span the entire 223 amino acid cathepsin G protein were synthesized. These eleven peptides were tested for antibacterial action against *N. gonorrhoeae*, *P. aeruginosa* and *S. aureus*. Of the eleven peptides, only the peptide corresponding to residues 117-136 in the full-length cathepsin G (CG 117-136) (SEQ ID NO:22) displayed antibacterial action against all three pathogens; 500 μg of peptide per ml killed 5-6 logs of *P. aeruginosa* and *S. aureus*. See Table 6 for the peptide sequences and activities, as measured using a crude peptide concentration of 500 μg/ml with an input viable cell concentration of about $10^7$ colony forming units/ml (CFU/ml) in 1/100 strength HBSS. CB117-136 will be useful as an antibacterial agent against a wide range of bacteria, including pathogens.

TABLE 6

| | | |
|---|---|---|
| Antibactericidal Activity of Crude Peptides[1] | | |
| | Log Kill (500 μg/ml) | |
| Peptide Sequence | *P. aeruginosa* ATCC 27853 | *N. gonorrhoeae* strain WS1 |
| 1                  20<br>IIGGRESRPHSRPYMAYLQI | 5.507 | 2.57 (SEQ ID NO: 16) |
| 21               40<br>QSPAGQSRCGGFLVREDFVL | −0.034 | 0.05 (SEQ ID NO: 17) |
| 41               60<br>TAAHCWGSNINVTLGAHNIQ | 0.5 | −0.09 (SEQ ID NO: 18) |
| 61               80<br>RRENTQQHITARRAIRHPQY | 5.15 | 0 (SEQ ID NO: 19) |
| 77               96<br>HPQYNQRTIQNDIMLLQLSR | 0.06 | 0.24 (SEQ ID NO: 20) |
| 97              116<br>RVRRNRNVNPVALPRAQEGL | 5.93 | −0.21 (SEQ ID NO: 21) |
| 117           136<br>RPGTLCTVAGWGRVSMRRGT | 5.88 | 2.38 (SEQ ID NO: 22) |
| 137           156<br>DTLREVQLRVQRDRQCLRIF | 0.01 | 0.43 (SEQ ID NO: 23) |
| 157           176<br>GSYDPRRQICVGDRRERKAA | 1.02 | −0.18 (SEQ ID NO: 24) |
| 177           197<br>FKGDSGGPLLCNNVAHGIVSY | −0.79 | 0.68 (SEQ ID NO: 25) |
| 198           223 | | |

TABLE 6-continued

Antibactericidal Activity of Crude Peptides[1]

| | Log Kill (500 µg/ml) | |
|---|---|---|
| Peptide Sequence | P. aeruginosa ATCC 27853 | N. gonorrhoeae strain WS1 |
| GKSSGVPPEVFTRFVSSFLPWIRTTMR | 5.73 | 0.78 (SEQ ID NO: 26) |
| Buffer | −0.139 | 0.07 |

[1]Peptides shown in Bold were purified by RP-HPLC and tested vs. *P. aeruginosa, N. gonorrhoeae* and *S. aureus* (see Table 7A).

Table 7A provides antimicrobial activities of peptides purified by RP-HPLC, determined as above. Only CG 117-136 (SEQ ID NO:22) exhibits high activity against *P. aeruqinosa, S. aureus* and *N. gonorrhoeae*. Table 7B discloses the $ED_{90}$ in µg/ml for the antibacterial peptides, as measured with *P. aeruqinosa* ATCC 27853 as above. $ED_{90}$ is the dose required to kill 90% of the input cells in 2 h at 37° C. in 1/100 strength HBSS, where the input viable cell concentration is about $10^7$ CFU/ml.

TABLE 7A

Antibacterial Action of RP-HPLC-Purified Peptides

| | Log Kill (500 µg/ml | | |
|---|---|---|---|
| Peptide | P. aeruginosa ATCC 278533 | N. gonorrhoeae strain WSI | S. aureus strain 8325-4 |
| CG 1-20 | 1.0 | 0.43 | 0.3 (SEQ ID NO: 16) |
| CG 61-80 | 5.15[1] | ND | 0.58 (SEQ ID NO: 19) |
| CG 97-116 | 0.22 | 0.2 | −0.1 (SEQ ID NO: 21) |
| CG 117-136 | 5.88[1] | 4.20 | 5.34 (SEQ ID NO: 22) |
| CG 198-223 | 5.73[1] | ND | 0.26 (SEQ ID NO: 26) |
| Buffer Control | −0.139 | −0.07 | −0.25 |

[1]Also active against four clinical isolates of *P. aeruginosa*
[2]Not determined

TABLE 7B

Potency of Synthetic Cathepsin G Peptides Against *P. aeruginosa*

| Synthetic Peptides | $ED_{90}$ (µg/ml) |
|---|---|
| CG 1-20 | 500 (SEQ ID NO: 16) |
| CG 61-80 | 75 (SEQ ID NO: 19) |
| CG 97-116 | >500 (SEQ ID NO: 21) |
| CG 117-136 | 15 (SEQ ID NO: 22) |
| CG 198-223 | 115 (SEQ ID NO: 26) |

It was noted that CG 1-20 (SEQ ID NO:16) and CG 97-116 (SEQ ID NO:21) were highly active as crude peptides, but exhibited much lower activity when purified by RP-HPLC. Without wishing to be bound by any particular hypothesis, the inventors suggest that the high activity in the crude peptide preparation is due to one or more residual blocking or substituent groups or some unidentified side reaction product generated during the hydrogen fluoride cleavage and/or post-synthetic work-up.

Those peptides which exhibited significant activity against *P. aeruginosa* ATCC 27853, were also tested against four independent clinical isolates. *P. aeruginosa* ATCC 27853 (American Type Culture Collection, Rockville, Md.) is the strain used for testing antimicrobial activity against *P. aeruginosa* unless otherwise noted. It is a standardized strain for antibiotic-susceptibility testing of pseudomonads (see, e.g., Code of Federal Regulations, Title 21, Part 460, 1987). CG 61-80 (SEQ ID NO:19) and CG 198-223 (SEQ ID NO:26 exhibited some variability in effectiveness for killing of clinical strains, but so far as tested, CG 117-136 (SEQ ID NO:22) appeared to be a highly effective bactericidal peptide for *P. aeruqinosa* as well as *N. gonorrhoeae* and *S. aureus* (see Tables 7A, 8). Agents effective against *P. aeruginosa* are needed in the art because multiple antibiotic resistance is quite common among clinical strains, and therefore resultant infections are often difficult to treat.

TABLE 8

Bactericidal Activity of HPLC-Purified Peptides Against *P. aeruginosa* Clinical Isolates

| | Log Reduction in Viability[1] | | | |
|---|---|---|---|---|
| P. aeruginosa | Control | CG 61-80 | CG 117-136 | CG 198-223 |
| ATCC 27853 | −0.14 | 5.49 | 5.95 | 5.35 |
| #385128 | −1.1 | 1.91 | 6.17 | 4.71 |
| #36152 | −0.89 | 4.86 | 5.38 | 4.28 |
| #27853 | −0.58 | 5.80 | 5.79 | 4.80 |
| #A-91-330-0347 | −0.41 | 4.11 | 6.40 | 1.17 |

[1]3–5 × $10^7$ CFU/ml of the designated strains were exposed to 500 µg/ml of HPLC-purified peptides in 1/100 strength BHSS (10 mm sodium phosphate, pH 7.0, 10 mM NaCl.

To further characterize the activity of CG 117-136, a "D-enantiomer," composed only of D-amino acids but in the same sequence, was synthesized and tested for antimicrobial activity. The L- and D-forms of this same amino acid sequence had equivalent bactericidal activity against both *P. aeruginosa* and *N. gonorrhoeae* (Table 9). This result suggests that killing does not require the recognition of a microbial target with a chiral center.

TABLE 9

The Antibacterial Capacity of CG 117-136 (SEQ ID NO: 22) is Independent of Stereochemistry

| | Log Kill[1] | |
|---|---|---|
| Peptide | P. aeruginosa ATCC 27853 | N. gonorrhoeae strain WS1 |
| L-enantiomer | 5.62 | 4.20 |
| D-enantiomer | 5.92 | 4.20 |

[1]*P. aeruqinosa* (3 × $10^7$ CFU/ml) was exposed to 125 µg/ml of each peptide, while *N. gonorrhoeae* (5 × $10^6$ CFU/ml) was exposed to 500 µg/ml of each peptide.

Figure 2A:
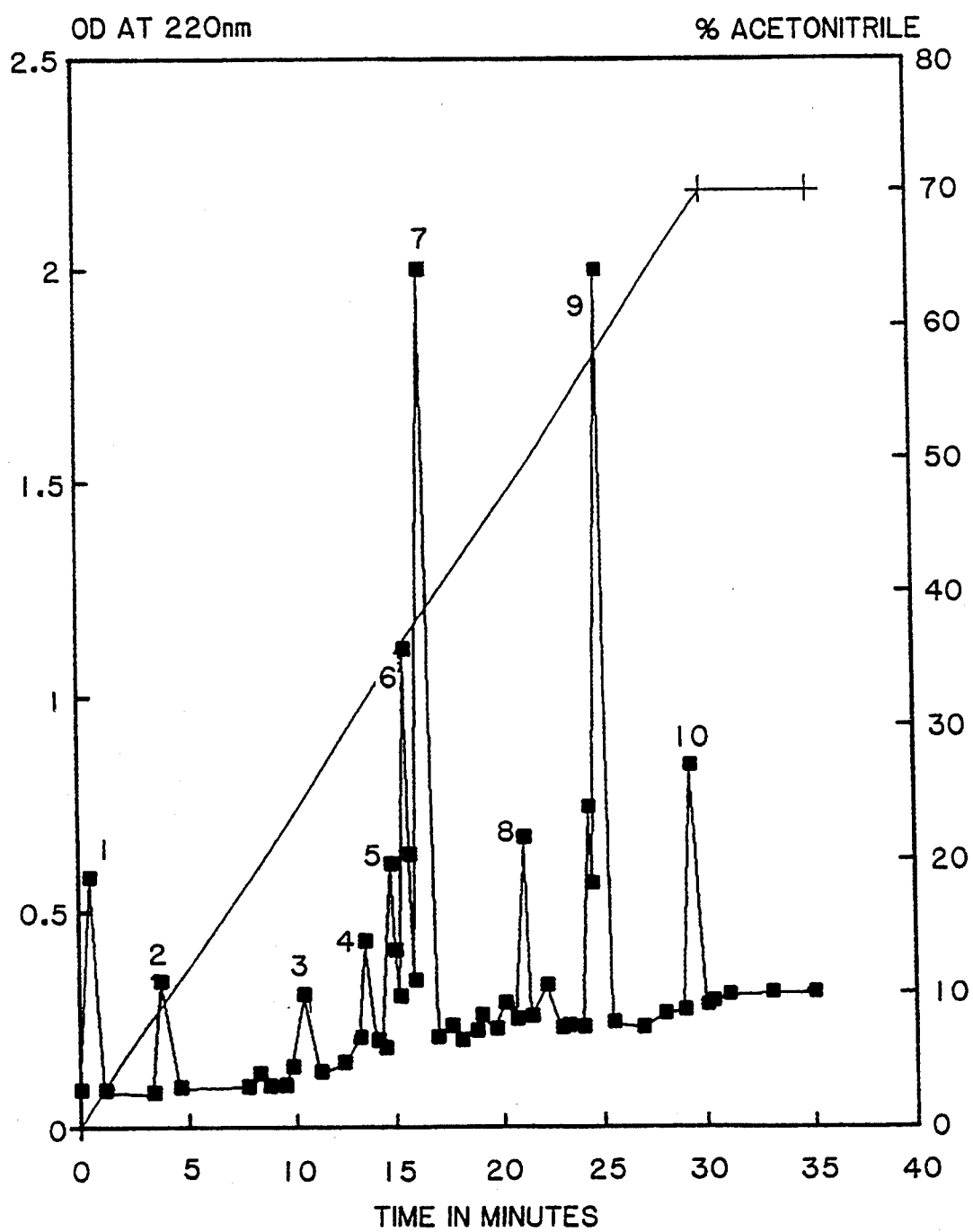
FIG. 2(A), cathepsin G digest fractionation.
Figure 2B:
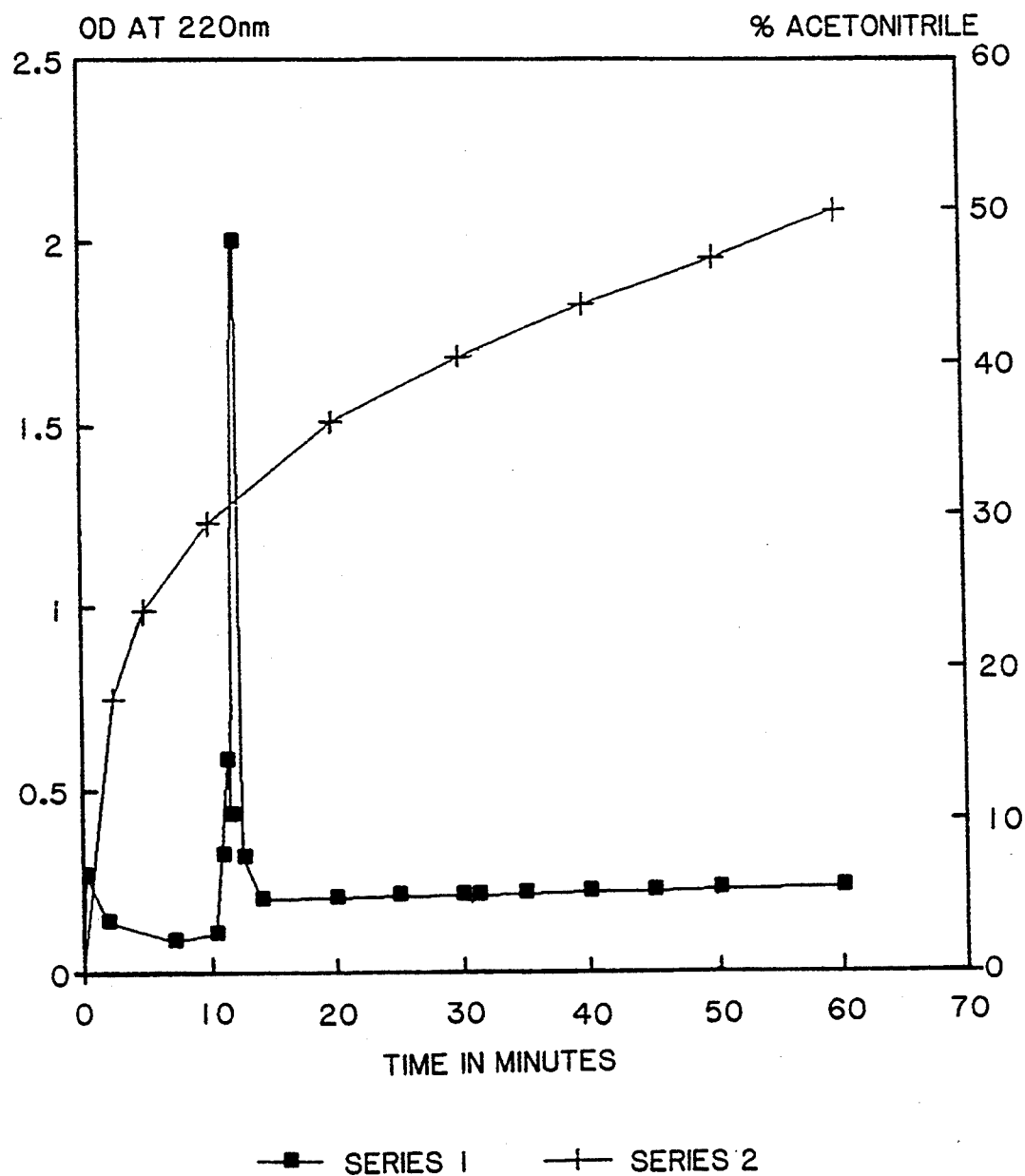
FIG. 2(B), rechromatography of peak 6.
Figure 2C:
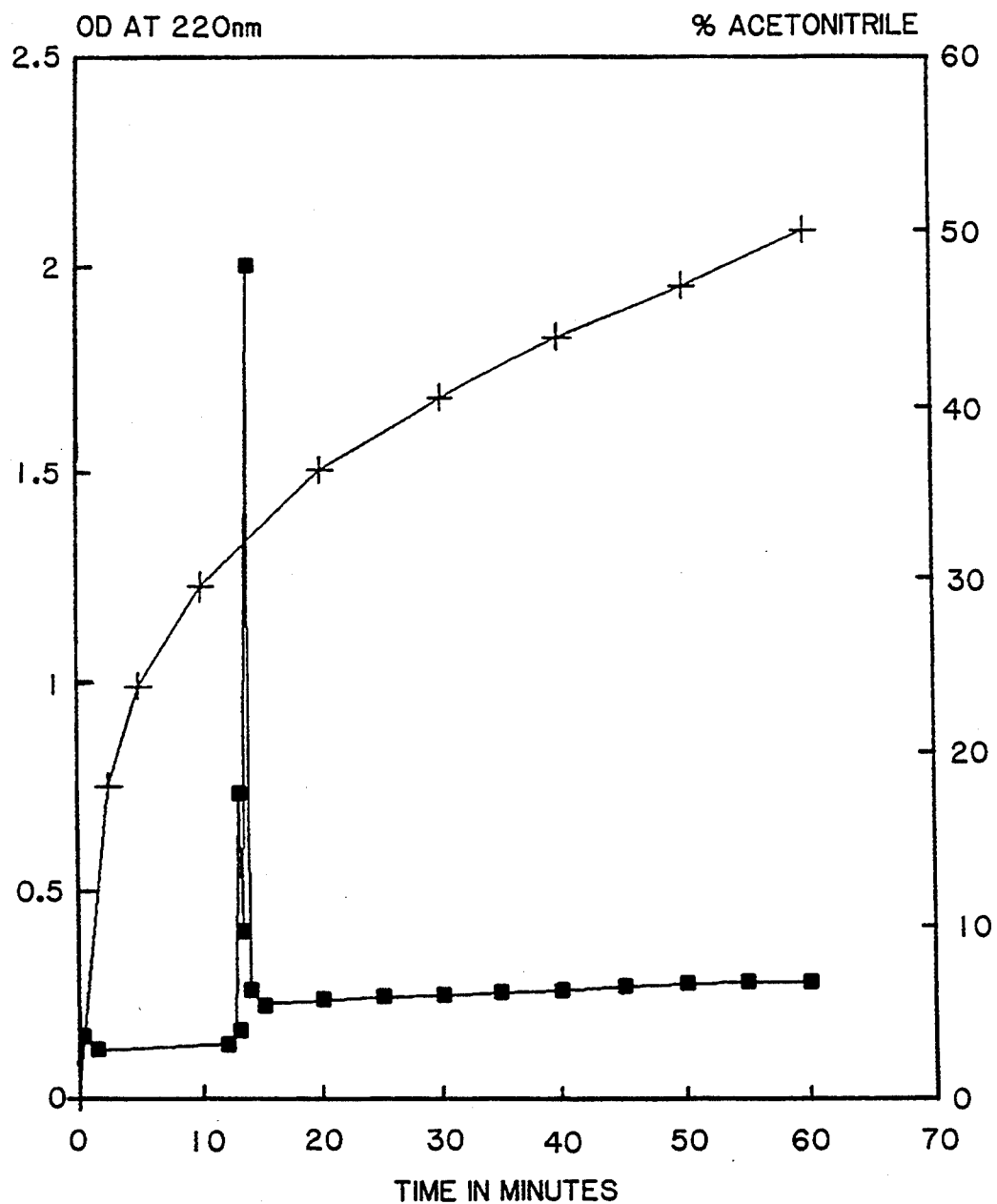
FIG. 2(C), rechromatography of peak 7.

As shown in FIG. 2B, CG 117-136 (SEQ ID NO:22) is predicted to have a hydrophobic domain in the N-terminal portion of the peptide and a cationic, hydrophilic domain in the C-terminal portion. The contribution(s) of these domains to antimicrobial activity was assessed by synthesizing truncated versions of CG 117-136. Both domains were required for full activity. Omission of either C-or N-terminal residues destroyed activity against *S. aureus*, while omission of the five N-terminal residues resulted in only about a 10-fold drop in activity for both *P. aeruginosa* and *N. gonorrhoeae*. Omission of the ten N-terminal residues caused nearly total loss of activity against *P. aeruqinosa* and a lesser reduction in activity as measured against *N. gonorrhoeae* (see Table 10A, 10B).

TABLE 10A

Summary of Domains in CG 117-136 and in Truncated CG 117-136 variants

| Peptide | Hydrophobic Domain | Hydrophilic Domain |
|---|---|---|
| CG 117-136 (SEQ. ID. NO: 22) | + | + |
| CG 117-129 (SEQ. ID. NO: 38) | + | − |
| CG 122-136 (SEQ. ID. NO: 39) | ± | + |
| CG 127-136 (SEQ. ID. NO: 40) | − | + |

TABLE 10B

Antibacterial Action of CG 117-136 and Truncated Variants of CG 117-136

| | Log Kill (500 µg/ml | | |
|---|---|---|---|
| Peptide | P. aeruginosa ATCC 27853 | N. gonorrhoeae strain WS1 | S. aureus strain 8325-4 |
| CG 117-136 (SEQ. ID NO: 22) | 5.8 | 4.20 | 5.34 |
| CG 117-129 (SEQ. ID NO: 38) | 0.86 | 0.05 | 0 |
| CG 122-136 (SEQ. ID NO: 39) | 4.75 | 4.18 | 0 |
| CG 127-136 (SEQ. ID NO: 40) | 0.27 | 3.20 | 0 |

The secondary structure of CG 117-136 (SEQ ID NO:22) has been predicted by computer analysis to exhibit β-Sheet structure. By contrast, several peptides known to interrupt the gram-negative envelope are α-helical peptides (See, e.g., Vaara, M. (1992) Microbiological Rev. 56:395–411).

The potent antibacterial peptide CG 117-136 (SEQ ID NO:22) displays partial significant sequence identities with other serine proteases or serine protease-like proteins (FIG. 10), termed serpocidins, based on their toxic action against bacteria and eucaryotic cells. The mechanism of cytotoxicity has not been defined, but it is likely that the serpocidins behave as membrane-disorganizing agents. Electron microscopic analysis of CG 117-136-treated *P. aeruginosa* cells revealed similar effects on cell morphology to those seen after treatment with polycationic agents. Lysis did not result from CG 117-136 treatment.

A comparison of the amino acid sequence of CG 117-136 (SEQ ID NO:22) to partial sequences of other antimicrobial proteins and serine proteases is given in FIG. 10. The dots represent amino acid identity. The skilled artisan can readily identify variants of the CG 117-136 sequence (or of other antibacterial peptides disclosed herein) by synthesizing defined variants and testing as taught herein.

The sensitivities of the *P. aeruginosa* and *S. aureus* indicator cells to enzymatically-active and inactive Cat G were determined (see Table 11). Surprisingly, peptides (CG 61-80, CG 117-136, CG 198-223) (SEQ ID NO:19, 21, 26, respectively) from cathepsin G display potent bactericidal action in vitro even against a pathogen (*P. aeruginosa*) that is killed only by enzymatically active Cat G.

TABLE 11

Bactericidal Capacities of Enzymatically-Active and -Inactive Cathepsin G

| | Log Reduction in CFU/ml[1] | |
|---|---|---|
| | S. aureus | P. aeruginosa |
| Control | −0.18 | −0.76 |
| 50 µg/ml enzymatically active Cat G | 2.82 | 2.41 |
| 50 µg/ml DFP-treated Cat G | 2.93 | 0.125 |

[1]Approximately 5 × 10⁶ CFU/ml of the test bacteria were incubated with the cathepsin G samples in 1% (w/v) TSB (tryticase soy broth) for 2 h at 37° C. The results are average values from 2 determinations for each strain and preparation of cathepsin G.

Only enzymatically-active cathepsin G kills *P. aeruqinosa*, while other pathogens are readily killed by both active and inactive cathepsin G. It is theorized that in order for the antibacterial peptides to properly interact with the pseudomonad cell envelope, the structure of the active site must be in its native state in order to allow accessibility of bactericidal domains in the full-length molecule or promote liberation of bactericidal fragments the full-length molecule by a mechanism such as bacterial protease action or by autoproteolysis, but the inventors do not wish to be bound by this theory. The results disclosed herein support the notion that bactericidal serine esterases possess broad spectrum antibacterial action due to the presence of internal antibacterial domains and that multiple, distinct domains exist within cathepsin G for the purpose of killing different pathogens.

The following examples are provided for illustrative purposes and are not intended to limit the scope of the invention. Because modification of the examples below will be apparent to those of skill in the art, it is intended that this invention be limited only by the scope of the appended claims. All references cited in this application are hereby incorporated by reference herein.

EXAMPLES

Example 1.1

Purification of Cat G and Human Neutrophil Elastase

Cat G and human neutrophil elastase (HLE) were purified from extracts of human PMN granules as described previously (Baugh and Travis (1976) Biochemistry 15:836–841). After purification, each enzyme was stored at −20° C. in 50 mM sodium acetate (pH 5.5) 0.5M NaCl prior to use.

Example 1.2

Clostripain Digestion of Cathepsin G

Cat G (600 micrograms) was incubated with purified clostripain (Sigma Chemical Company, St. Louis, Mo.) at a molar ratio of 50:1 in 50 mM Tris-HCl (pH 7.5) 10 mM CaCl₂ 0.16M NaCl 2.5 mM Dithiothreitol at 37° C. for 24 hours. During the incubation period samples were removed at various times and assayed for enzymatic and/or bacterial activity.

The enzymatic digestion of Cat G was monitored by loss of esterase activity using the synthetic substrate (Suc-L-Ala-L-Ala-Pro-Phe-pNA (Nakajima et al. (1979) J. Biol. Chem. 254:4027–4032). In some instances digestion was monitored by SDS polyacrylamide gel electrophoresis (Laemmli (1970) Nature (London) 227:680–685). Cat G was tested for antimicrobial activity as described in Shafer et al. (1986) Infect. Immun. 54:184–188.

Example 1.3

Isolation Of Cat G Peptides from Clostripain Digest

Clostripain (Mr 30 kDa) and undigested Cat G were separated from the degradation peptides by loading the 24 h digestion mixture (1.0 ml) on a Sephadex G-50 TM (Pharmacia Fine Chemicals, Piscataway, N.J.) column which was equilibrated with 1.0M $NH_{40}H$. Absorbances at 220 nm and 280 nm were monitored and those fractions containing peptides were pooled, lyophilized and dissolved in 0.1% trifluoroacetic acid (TFA).

The peptide mixture was then applied to a reverse phase HPLC (RP-HPLC) C-18-10 column which had been previously equilibrated with 0.1% TFA. Bound peptides were then eluted using a linear gradient of acetonitrile (0 to 70% (v/v)) in 0.1% TFA at a flow rate of 0.5 ml/min. Fractions were lyophilized for subsequent testing in antimicrobial assays. Fractions with bactericidal activity were reapplied to the RP-HPLC C-18-10 column. The bound peptides were eluted with non-linear gradient of acetonitrile (0 to 50% v/v) in 0.1% TFA with a flow rate of 0.5 ml/h. The elution of peptides was monitored by following $A_{220}$. Peptide concentrations were measured using ninhydrin as described (Rosen et al. (1962) Anal. Biochem. 4:213–221).

Example 1.4

Antimicrobial Activity Testing

*Neisseria gonorrhoeae* strain FA 102 and *Staphylococcus aureus* strain 8325-4 were the test bacteria used in many experiments; these strains have been described previously (Shafer et al. (1986) supra; Shafer and Onunka (1989) J. Gen. Microbiol. 135:825–830). *N. gonorrhoeae* were passaged on clear typing agar as non-piliated, transparent variants. For testing, cultures were grown with shaking at 37° C. in GC broth containing glucose, iron and sodium bicarbonate supplements. *S. aureus* was grown at 37° C. with shaking in LB broth. At midlogarithmic phase ($OD_{550}$ of 0.35) the cultures were diluted in Hanks Balanced Salt Solution (HBSS) (Gibco Laboratories, Grand Island, N.Y.) (pH 7.5) to give approximately $10^5$ CFU/ml. In other experiments, *P. aeruginosa* ATCC 27853, a standard antibiotic tester strain, was used.

Peptides were dissolved in HBSS (pH 7.5) and added in various amounts (0 to 100 micrograms) to sterile microtiter wells. After UV sterilization of the wells, 0.1 ml samples of the bacterial were added and the volumes in each well were adjusted with HBSS to 0.2 ml. The bacteria-peptide mixtures were incubated at 37° C. for 45–60 min unless otherwise noted. For *N. gonorrhoeae*, incubation was carried out under an atmosphere of 5% $CO_2$. In other experiments, as noted, 1/100 strength HBSS was used. For at least some strains, the use of 1/100 HBSS resulted in greater sensitivity to the bactericidal activity of the peptides disclosed herein.

Viability was determined after incubation by plating 10 and 100 microliter samples on LB agar (*S. aureus*) or GCB agar (*N. gonorrhoeae*). All assays were done in duplicate or triplicate, and the results given are the means of three independent experiments. The % survival of the test bacteria was calculated as 100×(# CFU in the presence of peptide)/(# CFU in the absence of peptide); standard error of the mean for each data point was never greater than 5%.

Certain antibiotics were tested for antibacterial activity using the procedure described above. Penicillin G, tetracycline, chloraphenicol, streptomycin and kanamycin (Sigma Chemical Company, St. Louis, Mo.) were each dissolved in distilled water or 50% (v/v) methanol to give a 1 mg/ml solution. All antibiotic solutions were stored at −20° C.

A partially purified preparation containing the three human defensins described by Selsted et al. (1985) J. Clin. Invest. 76:1436–1439, was also used in the antibacterial activity testing protocol described above. This preparation was provided by Dr. John Spitznagel, Emory University School of Medicine, Atlanta, Ga.). The preparation was obtained by Sephadex G-75 TM (Pharmacia, Piscataway, N.J.) chromatography of a crude acid extract of human PMN granules (Shafer et al. (1988) Infect. Immun. 56:51–53). The mixture of the three defensins eluted from the column after lysozyme (Mr 14.4 kDa), as is consistent with their molecular weights of approximately 5 kDa. Before use in the antibacterial activity test, the pooled defensins were dialyzed against 4 liters of distilled water at 4° C. using dialysis tubing with an exclusion limit of 3 kDa.

Example 1.5

Sequence analysis of Antibacterial Peptides

The sequences of the antibacterial peptides from clostripain digestion and HPLC resolution were determined by automated Edman degradation in a Model 477A Pulse Liquid Sequencer (Applied Biosystems, Inc., Foster City, Calif.), and the PTH-amino acids were identified on-line in a 120A PTH Analyzer (Applied Biosystems, Inc.).

Example 2

Preparation of Synthetic peptides

Oligopeptides were synthesized using an Applied Biosystems Model 430A peptide synthesizer (0.1–0.5 mmol scale) using phenylacetamidomethyl (Pam) or p-methylbenzyhydrylamine copoly(styrene/divinylbenzene) resins (Applied Biosystems, Inc., Foster City, Calif.) and tert-butyloxycarbonyl (Boc)-protected amino acids (Applied Biosystems, Inc. or Bachem, Inc., Torrance, Calif.). Boc-N-methyl-Ala, Boc-Arg (tosyl) or Boc-Arg (mesitylenesulfonyl), Boc-Asp (benzyl), Boc-Cys (4-methoxybenzyl), Boc-Glu (benzyl), Boc-His (benzyloxycarbonyl) or Boc-His (2,4-dinitrophenyl), Boc-DHis(4-toluenesulfonyl), Boc-Lys(chlorobenzyloxycarbonyl), Boc-Met, Boc-Ser (benzyl), Boc-Thr (benzyl), Boc-Trp or Boc-Trp (formyl), and Boc-Tyr (2-bromobenzyloxycarbonyl) were used for the incorporation of the respective amino acid residues. Boc-His(methyl) was incorporated in a manual mode on a 0.02 mmol scale using the N,N-dicyclohexylcarbodiimide/1-hydroxybenzotriazole coupling protocol. All amino acids (except glycine) used herein have the L configuration unless otherwise noted.

Peptides were cleaved from the resin and deprotected in liquid HF/p-cresol/dimethyl sulfide (10:1:0.5) at −5° C. for 90 min, or in liquid HF/anisole (9:1, v/v) at 0° C. for 90 min. The resins were washed with cold diethyl ether, and the peptides were extracted into 1.0M acetic acid and lyophilized. Peptides were then purified by RP-HPLC on an Aquapore TM RP-300 C18 silica column (1×10 cm, Applied Biosystems, Inc.), or on an MRPH-Gel TM polystyrene column (1×10 cm, The Nest Group, Scarborough, Mass.) using a 0–60% linear gradient of acetonitrile in 0.1% TFA. The purity of each synthetic peptide preparation was confirmed by microbore HPLC on Aquapore TM OD-300 columns of C18 silica (1×250 mm, Applied Biosystems, Inc.), quantitative amino acid analysis and sequencing, as described above. Peptides were generally stored in the lyophilized form at 4° C. prior to use in the antibacterial assays.

It is understood in the art that there are other suitable peptide synthetic devices or that manual peptide synthesis could be carried out to produce the peptides of the present invention. Automated solid phase peptide synthesis is described, e.g., in Stewart et al. (1984) *Solid Phase peptide Synthesis,* Pierce Chemical Company, Rockford, Ill.).

Example 3

Search for Related Peptide Sequences

A search was done on protein computer databases using the HPQYNQR sequence for similar sequences in other proteins. Sequences with some similarity to this Cat G sequence were recognized in certain other cytotoxic proteases. Searches were also done using the IIGGR sequence (SEQ ID NO:1) and the CG 117–136 sequence (SEQ ID NO:22).

The antimicrobial peptides of the present invention will be useful for inhibiting bacterial growth for research, including in vitro culture applications, and, when formulated into therapeutic compositions, will be useful in the treatment of infections, especially bacterial infections. The antimicrobial peptides can be administered by any mechanism known to the art, as appropriate for a particular type of infection.

We claim:

1. a peptide having antimicrobial activity, said peptide having a length of from five amino acids up to twenty-six amino acids, and which peptide comprises a sequence selected from the group of amino acid sequences consisting of IIGGR (SEQ ID NO:1), IVGGR (SEQ ID NO:2) and HPQYNQR (SEQ ID NO:3).

2. A therapeutic composition for controlling infection by a bacterium, said composition comprising at least one antimicrobial peptide of claim 1 and a pharmacologically acceptable carrier, wherein said bacterium is sensitive to the antimicrobial activity of said peptide.

3. A peptide having antimicrobial activity, said peptide having from ten to twenty-seven amino acids, and said peptide having an amino acid sequence selected from the group of amino acid sequences consisting of IIGGRESRPHSRPYMAYLQI (SEQ ID NO:16), RRENTQQHITARRAIRHPQY (SEQ ID NO:19), RPGTLCTVAGWGRVSMRRGT (SEQ ID NO:19), GKSSGVPPEVFTRFVSSFLPWIRTTMR (SEQ ID NO:26), CTVAGWGRVSMRRGT (SEQ ID NO:39), WSRVSMRRGT (SEQ ID NO:40) and RPGTLCTVAGWGRVSMRRGT, wherein each amino acid of the latter is in the D-configuration.

4. A therapeutic composition for controlling infection by a bacterium, said composition comprising at least one antimicrobial peptide of claim 3 and a pharmacologically acceptable carrier, wherein said bacterium is sensitive to the antimicrobial activity of said peptide.

* * * * *

UNITED STATES PATENT AND TRADEMARK OFFICE
CERTIFICATE OF CORRECTION

PATENT NO. : 5,447,914

DATED : September 5, 1995

INVENTOR(S) : James Travis, William M. Shafer, Neelesh Bangalore and Jan Pohl

It is certified that error appears in the above-indentified patent and that said Letters Patent is hereby corrected as shown below:

On the title page: Item [56] Reference Cited: add the following

Baugh, R. and J. Travis (1976) *Biochemistry* 15:836-841.

Drazin, R. and R. Lehrer (1977) *Infect. Immunol.* 17:382-388.

Gabay et al. (1989) *Proc. Natl. Acad. Sci. USA* 86:5610-5614.

Ganz et al. (1986) *Sem. Respirat. Infect.* 1:107-117.

Gleich et al. (1986) *Proc. Natl. Acad. Sci. USA* 83:3146-3150.

Jenne et al. (1989) *Biochemistry* 28:7953-7961.

Jenne, D. and J. Tschopp (1988) *Immunol. Rev.* 103:53-71.

Odeberg, H. and I. Olsson (1975) *J. Clin. Invest.* 56:1118-1124.

Pereira et al. (1990) *J. Clin. Invest.* 85:1468-1476.

Pollock et al. U.S. Patent No. 4,725,576, issued February 16, 1988.

Salvesen et al. (1987) *Biochemistry* 26:2289-2293.

Selsted et al. (1985) *J. Clinical Invest.* 76:1436-1439.

UNITED STATES PATENT AND TRADEMARK OFFICE
CERTIFICATE OF CORRECTION

PATENT NO. : 5,447,914
DATED : September 5, 1995
INVENTOR(S) : James Travis, William M. Shafer, Neelesh Bangalore and Jan Pohl It is certified that error appears in the above-indentified patent and that said Letters Patent is hereby corrected as shown below:

Shafer et al. (1986) *Infect. Immunol.* 54:184-188.

Shafer et al. (1988) *Infect. Immunol.* 56:51-53.

Shafer, W. and V. Onunka (1989) *J. Gen. Microbiol.* 135:825-830.

Sinha et al. (1987) *Proc. Natl. Acad. Sci. USA* 84:2228-2232.

At column 21, line 6, please rewrite "$NH_{40}H$." as --$NH_4OH$.--. This recitation correctly appears in the as-filed patent application at page 41, line 6.

In claim 3, at column 50, line 45, please rewrite "WSRVSMRRGT" as --WGRVSMRRGT--. The correct recitation was presented in Applicants' amendment filed in the Patent and Trademark Office on February 15, 1995.

Signed and Sealed this

Thirteenth Day of February, 1996

*Attest:*

BRUCE LEHMAN

*Attesting Officer*     *Commissioner of Patents and Trademarks*

SEQUENCE LISTING ( 1 ) GENERAL INFORMATION:

( i i i ) NUMBER OF SEQUENCES: 59

( 2 ) INFORMATION FOR SEQ ID NO:1:

( i ) SEQUENCE CHARACTERISTICS:
        ( A ) LENGTH: 5 amino acids
        ( B ) TYPE: amino acid
        ( C ) STRANDEDNESS: single
        ( D ) TOPOLOGY: linear ( i i ) MOLECULE TYPE: peptide ( x i ) SEQUENCE DESCRIPTION: SEQ ID NO:1:

Ile Ile Gly Gly Arg
    1                    5

( 2 ) INFORMATION FOR SEQ ID NO:2:

( i ) SEQUENCE CHARACTERISTICS:
        ( A ) LENGTH: 5 amino acids
        ( B ) TYPE: amino acid
        ( C ) STRANDEDNESS: single
        ( D ) TOPOLOGY: linear ( i i ) MOLECULE TYPE: peptide ( x i ) SEQUENCE DESCRIPTION: SEQ ID NO:2:

Ile Val Gly Gly Arg
    1                    5

( 2 ) INFORMATION FOR SEQ ID NO:3:

( i ) SEQUENCE CHARACTERISTICS:
        ( A ) LENGTH: 7 amino acids
        ( B ) TYPE: amino acid
        ( C ) STRANDEDNESS: single
        ( D ) TOPOLOGY: linear ( i i ) MOLECULE TYPE: peptide ( x i ) SEQUENCE DESCRIPTION: SEQ ID NO:3:

His Pro Gln Tyr Asn Gln Arg
    1                    5

( 2 ) INFORMATION FOR SEQ ID NO:4:

( i ) SEQUENCE CHARACTERISTICS:
        ( A ) LENGTH: 7 amino acids
        ( B ) TYPE: amino acid
        ( C ) STRANDEDNESS: single
        ( D ) TOPOLOGY: linear (i i) MOLECULE TYPE: peptide (i x) FEATURE:
        (A) NAME/KEY: Region
        (B) LOCATION: 2..3
        (D) OTHER INFORMATION: /label=Xaa
            / note="X at position 2 is Pro, His or Ala."

(i x) FEATURE:
        (A) NAME/KEY: Peptide
        (B) LOCATION: 1..3
        (D) OTHER INFORMATION: /product="OTHER"
            / label=Xaa
            / note="X at position 3 is Asp, Asn, Glu, Gln, Ala, Ser, Thr, Ile, Val, Tyr, Arg, Methionin Oxide or Methionine Sulfone."

(i x) FEATURE:
        (A) NAME/KEY: Region
        (B) LOCATION: 3..4
        (D) OTHER INFORMATION: /product="OTHER"
            / label=Xaa
            / note="X at position 4is Tyr, Phe, Trp or Beta- naphthyl-alanine."

(i x) FEATURE:
        (A) NAME/KEY: Region
        (B) LOCATION: 4..5
        (D) OTHER INFORMATION: /product="OTHER"
            / label=Xaa
            / note="X at position 5 is Ala or Asn."

(i x) FEATURE:
        (A) NAME/KEY: Region
        (B) LOCATION: 5..6
        (D) OTHER INFORMATION: /product="OTHER"
            / label=Xaa
            / note="X at position 6 is Gln, Pro, Ala or N-methyl- alanine."

(i x) FEATURE:
        (A) NAME/KEY: Region
        (B) LOCATION: 6..7
        (D) OTHER INFORMATION: /product="OTHER"
            / label=Xaa
            / note="X at position 7 is Arg, Lys, Ala, NH2 or OH."

(x i) SEQUENCE DESCRIPTION: SEQ ID NO:4:

His  Xaa  Xaa  Xaa  Xaa  Xaa  Xaa
    1                    5

(2) INFORMATION FOR SEQ ID NO:5:

(i) SEQUENCE CHARACTERISTICS:
        (A) LENGTH: 7 amino acids
        (B) TYPE: amino acid
        (C) STRANDEDNESS: single
        (D) TOPOLOGY: linear (i i) MOLECULE TYPE: peptide (x i) SEQUENCE DESCRIPTION: SEQ ID NO:5:

His  Pro  Ala  Tyr  Asn  Pro  Lys
    1                    5

(2) INFORMATION FOR SEQ ID NO:6:

(i) SEQUENCE CHARACTERISTICS:
        (A) LENGTH: 7 amino acids
        (B) TYPE: amino acid
        (C) STRANDEDNESS: single
        (D) TOPOLOGY: linear (i i) MOLECULE TYPE: peptide (x i) SEQUENCE DESCRIPTION: SEQ ID NO:6:

His  Pro  Ala  Tyr  Asn  Pro  Arg (2) INFORMATION FOR SEQ ID NO:7:

(i) SEQUENCE CHARACTERISTICS:
        (A) LENGTH: 7 amino acids
        (B) TYPE: amino acid
        (C) STRANDEDNESS: single
        (D) TOPOLOGY: linear (ii) MOLECULE TYPE: peptide (xi) SEQUENCE DESCRIPTION: SEQ ID NO:7:

His Pro Ala Tyr Asn Gln Arg
    1               5

(2) INFORMATION FOR SEQ ID NO:8:

(i) SEQUENCE CHARACTERISTICS:
        (A) LENGTH: 7 amino acids
        (B) TYPE: amino acid
        (C) STRANDEDNESS: single
        (D) TOPOLOGY: linear (ii) MOLECULE TYPE: peptide (xi) SEQUENCE DESCRIPTION: SEQ ID NO:8:

His Pro Gln Tyr Ala Gln Arg
    1               5

(2) INFORMATION FOR SEQ ID NO:9:

(i) SEQUENCE CHARACTERISTICS:
        (A) LENGTH: 7 amino acids
        (B) TYPE: amino acid
        (C) STRANDEDNESS: single
        (D) TOPOLOGY: linear (ii) MOLECULE TYPE: peptide (xi) SEQUENCE DESCRIPTION: SEQ ID NO:9:

His Pro Gln Tyr Asn Gln Ala
    1               5

(2) INFORMATION FOR SEQ ID NO:10:

(i) SEQUENCE CHARACTERISTICS:
        (A) LENGTH: 7 amino acids
        (B) TYPE: amino acid
        (C) STRANDEDNESS: single
        (D) TOPOLOGY: linear (ii) MOLECULE TYPE: peptide (xi) SEQUENCE DESCRIPTION: SEQ ID NO:10:

His Pro Gln Tyr Asn Ala Arg
    1               5

(2) INFORMATION FOR SEQ ID NO:11:

(i) SEQUENCE CHARACTERISTICS:
        (A) LENGTH: 7 amino acids
        (B) TYPE: amino acid
        (C) STRANDEDNESS: single
        (D) TOPOLOGY: linear (ii) MOLECULE TYPE: peptide (xi) SEQUENCE DESCRIPTION: SEQ ID NO:11:

His Ala Gln Tyr Asn Gln Arg
    1               5

( 2 ) INFORMATION FOR SEQ ID NO:12:

( i ) SEQUENCE CHARACTERISTICS:
        ( A ) LENGTH: 6 amino acids
        ( B ) TYPE: amino acid
        ( C ) STRANDEDNESS: single
        ( D ) TOPOLOGY: linear ( i i ) MOLECULE TYPE: peptide ( x i ) SEQUENCE DESCRIPTION: SEQ ID NO:12:

```
His  Pro  Gln  Tyr  Asn  Gln
1                  5
```

( 2 ) INFORMATION FOR SEQ ID NO:13:

( i ) SEQUENCE CHARACTERISTICS:
        ( A ) LENGTH: 8 amino acids
        ( B ) TYPE: amino acid
        ( C ) STRANDEDNESS: single
        ( D ) TOPOLOGY: linear ( i i ) MOLECULE TYPE: peptide ( x i ) SEQUENCE DESCRIPTION: SEQ ID NO:13:

```
Arg  His  Pro  Gln  Tyr  Asn  Gln  Arg
1                  5
```

( 2 ) INFORMATION FOR SEQ ID NO:14:

( i ) SEQUENCE CHARACTERISTICS:
        ( A ) LENGTH: 20 amino acids
        ( B ) TYPE: amino acid
        ( C ) STRANDEDNESS: single
        ( D ) TOPOLOGY: linear ( i i ) MOLECULE TYPE: peptide ( x i ) SEQUENCE DESCRIPTION: SEQ ID NO:14:

```
His  Pro  Gln  Tyr  Asn  Gln  Arg  Thr  Ile  Gln  Asn  Asp  Ile  Met  Leu  Leu
1                  5                            10                           15

Gln  Leu  Ser  Arg
                20
```

( 2 ) INFORMATION FOR SEQ ID NO:15:

( i ) SEQUENCE CHARACTERISTICS:
        ( A ) LENGTH: 7 amino acids
        ( B ) TYPE: amino acid
        ( C ) STRANDEDNESS: single
        ( D ) TOPOLOGY: linear ( i i ) MOLECULE TYPE: peptide ( x i ) SEQUENCE DESCRIPTION: SEQ ID NO:15:

```
Ala  Pro  Gln  Tyr  Asn  Gln  Arg
1                  5
```

( 2 ) INFORMATION FOR SEQ ID NO:16:

( i ) SEQUENCE CHARACTERISTICS:
        ( A ) LENGTH: 20 amino acids
        ( B ) TYPE: amino acid
        ( C ) STRANDEDNESS: single
        ( D ) TOPOLOGY: linear ( i i ) MOLECULE TYPE: peptide ( x i ) SEQUENCE DESCRIPTION: SEQ ID NO:16:

```
Ile  Ile  Gly  Gly  Arg  Glu  Ser  Arg  Pro  His  Ser  Arg  Pro  Tyr  Met  Ala
1                  5                            10                           15
```

```
            Tyr  Leu  Gln  Ile
                       20
```

(2) INFORMATION FOR SEQ ID NO:17:

(i) SEQUENCE CHARACTERISTICS:
        (A) LENGTH: 20 amino acids
        (B) TYPE: amino acid
        (C) STRANDEDNESS: single
        (D) TOPOLOGY: linear (ii) MOLECULE TYPE: peptide (xi) SEQUENCE DESCRIPTION: SEQ ID NO:17:

```
Gln  Ser  Pro  Ala  Gly  Gln  Ser  Arg  Cys  Gly  Gly  Phe  Leu  Val  Arg  Glu
 1              5                        10                           15

Asp  Phe  Val  Leu
              20
```

(2) INFORMATION FOR SEQ ID NO:18:

(i) SEQUENCE CHARACTERISTICS:
        (A) LENGTH: 20 amino acids
        (B) TYPE: amino acid
        (C) STRANDEDNESS: single
        (D) TOPOLOGY: linear (ii) MOLECULE TYPE: peptide (xi) SEQUENCE DESCRIPTION: SEQ ID NO:18:

```
Thr  Ala  Ala  His  Cys  Trp  Gly  Ser  Asn  Ile  Asn  Val  Thr  Leu  Gly  Ala
 1              5                        10                           15

His  Asn  Ile  Gln
              20
```

(2) INFORMATION FOR SEQ ID NO:19:

(i) SEQUENCE CHARACTERISTICS:
        (A) LENGTH: 20 amino acids
        (B) TYPE: amino acid
        (C) STRANDEDNESS: single
        (D) TOPOLOGY: linear (ii) MOLECULE TYPE: peptide (xi) SEQUENCE DESCRIPTION: SEQ ID NO:19:

```
Arg  Arg  Glu  Asn  Thr  Gln  Gln  His  Ile  Thr  Ala  Arg  Arg  Ala  Ile  Arg
 1              5                        10                           15

His  Pro  Gln  Tyr
              20
```

(2) INFORMATION FOR SEQ ID NO:20:

(i) SEQUENCE CHARACTERISTICS:
        (A) LENGTH: 20 amino acids
        (B) TYPE: amino acid
        (C) STRANDEDNESS: single
        (D) TOPOLOGY: linear (ii) MOLECULE TYPE: peptide (xi) SEQUENCE DESCRIPTION: SEQ ID NO:20:

```
His  Pro  Gln  Tyr  Asn  Gln  Arg  Thr  Ile  Gln  Asn  Asp  Ile  Met  Leu  Leu
 1              5                        10                           15

Gln  Leu  Ser  Arg
              20
```

(2) INFORMATION FOR SEQ ID NO:21:

( i ) SEQUENCE CHARACTERISTICS:
    ( A ) LENGTH: 20 amino acids
    ( B ) TYPE: amino acid
    ( C ) STRANDEDNESS: single
    ( D ) TOPOLOGY: linear ( i i ) MOLECULE TYPE: peptide ( x i ) SEQUENCE DESCRIPTION: SEQ ID NO:21:

Arg Val Arg Arg Asn Arg Asn Val Asn Pro Val Ala Leu Pro Arg Ala
1               5                   10                  15

Gln Glu Gly Leu
            20

( 2 ) INFORMATION FOR SEQ ID NO:22:

( i ) SEQUENCE CHARACTERISTICS:
    ( A ) LENGTH: 20 amino acids
    ( B ) TYPE: amino acid
    ( C ) STRANDEDNESS: single
    ( D ) TOPOLOGY: linear ( i i ) MOLECULE TYPE: peptide ( x i ) SEQUENCE DESCRIPTION: SEQ ID NO:22:

Arg Pro Gly Thr Leu Cys Thr Val Ala Gly Trp Gly Arg Val Ser Met
1               5                   10                  15

Arg Arg Gly Thr
            20

( 2 ) INFORMATION FOR SEQ ID NO:23:

( i ) SEQUENCE CHARACTERISTICS:
    ( A ) LENGTH: 20 amino acids
    ( B ) TYPE: amino acid
    ( C ) STRANDEDNESS: single
    ( D ) TOPOLOGY: linear ( i i ) MOLECULE TYPE: peptide ( x i ) SEQUENCE DESCRIPTION: SEQ ID NO:23:

Asp Thr Leu Arg Glu Val Gln Leu Arg Val Gln Arg Asp Arg Gln Cys
1               5                   10                  15

Leu Arg Ile Phe
            20

( 2 ) INFORMATION FOR SEQ ID NO:24:

( i ) SEQUENCE CHARACTERISTICS:
    ( A ) LENGTH: 20 amino acids
    ( B ) TYPE: amino acid
    ( C ) STRANDEDNESS: single
    ( D ) TOPOLOGY: linear ( i i ) MOLECULE TYPE: peptide ( x i ) SEQUENCE DESCRIPTION: SEQ ID NO:24:

Gly Ser Tyr Asp Pro Arg Arg Gln Ile Cys Val Gly Asp Arg Arg Glu
1               5                   10                  15

Arg Lys Ala Ala
            20

( 2 ) INFORMATION FOR SEQ ID NO:25:

( i ) SEQUENCE CHARACTERISTICS:
    ( A ) LENGTH: 21 amino acids
    ( B ) TYPE: amino acid
    ( C ) STRANDEDNESS: single
    ( D ) TOPOLOGY: linear (ii) MOLECULE TYPE: peptide (xi) SEQUENCE DESCRIPTION: SEQ ID NO:25:

Phe Lys Gly Asp Ser Gly Gly Pro Leu Leu Cys Asn Asn Val Ala His
1               5                   10                  15
Gly Ile Val Ser Tyr
            20

(2) INFORMATION FOR SEQ ID NO:26:

(i) SEQUENCE CHARACTERISTICS:
        (A) LENGTH: 27 amino acids
        (B) TYPE: amino acid
        (C) STRANDEDNESS: single
        (D) TOPOLOGY: linear (ii) MOLECULE TYPE: peptide (xi) SEQUENCE DESCRIPTION: SEQ ID NO:26:

Gly Lys Ser Ser Gly Val Pro Pro Glu Val Phe Thr Arg Phe Val Ser
1               5                   10                  15
Ser Phe Leu Pro Trp Ile Arg Thr Thr Met Arg
            20                  25

(2) INFORMATION FOR SEQ ID NO:27:

(i) SEQUENCE CHARACTERISTICS:
        (A) LENGTH: 7 amino acids
        (B) TYPE: amino acid
        (C) STRANDEDNESS: single
        (D) TOPOLOGY: linear (ii) MOLECULE TYPE: peptide (xi) SEQUENCE DESCRIPTION: SEQ ID NO:27:

Ala Pro Gln Tyr Asn Gln Arg
1               5

(2) INFORMATION FOR SEQ ID NO:28:

(i) SEQUENCE CHARACTERISTICS:
        (A) LENGTH: 5 amino acids
        (B) TYPE: amino acid
        (C) STRANDEDNESS: single
        (D) TOPOLOGY: linear (ii) MOLECULE TYPE: peptide (xi) SEQUENCE DESCRIPTION: SEQ ID NO:28:

Ile Ile Gly Gly His
1               5

(2) INFORMATION FOR SEQ ID NO:29:

(i) SEQUENCE CHARACTERISTICS:
        (A) LENGTH: 5 amino acids
        (B) TYPE: amino acid
        (C) STRANDEDNESS: single
        (D) TOPOLOGY: linear (ii) MOLECULE TYPE: peptide (xi) SEQUENCE DESCRIPTION: SEQ ID NO:29:

Ile Ile Gly Gly Val
1               5

(2) INFORMATION FOR SEQ ID NO:30:

(i) SEQUENCE CHARACTERISTICS:

(A) LENGTH: 7 amino acids
(B) TYPE: amino acid
(C) STRANDEDNESS: single
(D) TOPOLOGY: linear (ii) MOLECULE TYPE: peptide (xi) SEQUENCE DESCRIPTION: SEQ ID NO:30:

His Pro Gln Tyr Asn Pro Gln
1               5

(2) INFORMATION FOR SEQ ID NO:31:

(i) SEQUENCE CHARACTERISTICS:
(A) LENGTH: 7 amino acids
(B) TYPE: amino acid
(C) STRANDEDNESS: single
(D) TOPOLOGY: linear (ii) MOLECULE TYPE: peptide (xi) SEQUENCE DESCRIPTION: SEQ ID NO:31:

His His Gln Tyr Asn Gln Arg
1               5

(2) INFORMATION FOR SEQ ID NO:32:

(i) SEQUENCE CHARACTERISTICS:
(A) LENGTH: 7 amino acids
(B) TYPE: amino acid
(C) STRANDEDNESS: single
(D) TOPOLOGY: linear (ii) MOLECULE TYPE: peptide (xi) SEQUENCE DESCRIPTION: SEQ ID NO:32:

His Pro Gln Ala Asn Gln Arg
1               5

(2) INFORMATION FOR SEQ ID NO:33:

(i) SEQUENCE CHARACTERISTICS:
(A) LENGTH: 7 amino acids
(B) TYPE: amino acid
(C) STRANDEDNESS: single
(D) TOPOLOGY: linear (ii) MOLECULE TYPE: peptide (xi) SEQUENCE DESCRIPTION: SEQ ID NO:33:

His Pro Gln Lys Asn Thr Tyr
1               5

(2) INFORMATION FOR SEQ ID NO:34:

(i) SEQUENCE CHARACTERISTICS:
(A) LENGTH: 7 amino acids
(B) TYPE: amino acid
(C) STRANDEDNESS: single
(D) TOPOLOGY: linear (ii) MOLECULE TYPE: peptide (xi) SEQUENCE DESCRIPTION: SEQ ID NO:34:

His Pro Gln Phe Asn Gln Arg
1               5

(2) INFORMATION FOR SEQ ID NO:35:

(i) SEQUENCE CHARACTERISTICS:
(A) LENGTH: 7 amino acids
(B) TYPE: amino acid ( C ) STRANDEDNESS: single
( D ) TOPOLOGY: linear ( i i ) MOLECULE TYPE: peptide ( x i ) SEQUENCE DESCRIPTION: SEQ ID NO:35:

His Pro Asn Tyr Asn Gln Arg
1               5

( 2 ) INFORMATION FOR SEQ ID NO:36:

( i ) SEQUENCE CHARACTERISTICS:
( A ) LENGTH: 7 amino acids
( B ) TYPE: amino acid
( C ) STRANDEDNESS: single
( D ) TOPOLOGY: linear ( i i ) MOLECULE TYPE: peptide ( x i ) SEQUENCE DESCRIPTION: SEQ ID NO:36:

His Pro Glu Tyr Asn Gln Arg
1               5

( 2 ) INFORMATION FOR SEQ ID NO:37:

( i ) SEQUENCE CHARACTERISTICS:
( A ) LENGTH: 7 amino acids
( B ) TYPE: amino acid
( C ) STRANDEDNESS: single
( D ) TOPOLOGY: linear ( i i ) MOLECULE TYPE: peptide ( x i ) SEQUENCE DESCRIPTION: SEQ ID NO:37:

His Pro Leu Tyr Asn Gln Arg
1               5

( 2 ) INFORMATION FOR SEQ ID NO:38:

( i ) SEQUENCE CHARACTERISTICS:
( A ) LENGTH: 13 amino acids
( B ) TYPE: amino acid
( C ) STRANDEDNESS: single
( D ) TOPOLOGY: linear ( i i ) MOLECULE TYPE: peptide ( x i ) SEQUENCE DESCRIPTION: SEQ ID NO:38:

Arg Pro Gly Leu Thr Leu Cys Thr Val Ala Gly Trp Gly
1               5                   10

( 2 ) INFORMATION FOR SEQ ID NO:39:

( i ) SEQUENCE CHARACTERISTICS:
( A ) LENGTH: 15 amino acids
( B ) TYPE: amino acid
( C ) STRANDEDNESS: single
( D ) TOPOLOGY: linear ( i i ) MOLECULE TYPE: peptide ( x i ) SEQUENCE DESCRIPTION: SEQ ID NO:39:

Cys Thr Val Ala Gly Trp Gly Arg Val Ser Met Arg Arg Gly Thr
1               5                   10                  15

( 2 ) INFORMATION FOR SEQ ID NO:40:

( i ) SEQUENCE CHARACTERISTICS:
( A ) LENGTH: 10 amino acids
( B ) TYPE: amino acid
( C ) STRANDEDNESS: single
( D ) TOPOLOGY: linear ( i i ) MOLECULE TYPE: peptide ( x i ) SEQUENCE DESCRIPTION: SEQ ID NO:40:

Trp Gly Arg Val Ser Met Arg Arg Gly Thr
1               5                   10

( 2 ) INFORMATION FOR SEQ ID NO:41:

( i ) SEQUENCE CHARACTERISTICS:
( A ) LENGTH: 223 amino acids
( B ) TYPE: amino acid
( C ) STRANDEDNESS: single
( D ) TOPOLOGY: linear ( i i ) MOLECULE TYPE: peptide ( x i ) SEQUENCE DESCRIPTION: SEQ ID NO:41:

Ile Ile Gly Gly Arg Glu Ser Arg Pro His Ser Arg Pro Tyr Met Ala
1               5                   10                  15

Tyr Leu Gln Ile Gln Ser Pro Ala Gly Gln Ser Arg Cys Gly Gly Phe
                20              25                  30

Leu Val Arg Glu Asp Phe Val Leu Thr Ala Ala His Cys Trp Gly Ser
            35              40                  45

Asn Ile Asn Val Thr Leu Gly Ala His Asn Ile Asp Arg Arg Glu Asn
50                      55                  60

Thr Gln Gln His Ile Thr Ala Arg Arg Ala Ile Arg His Pro Gln Tyr
65                  70                  75                  80

Asn Gln Arg Thr Ile Gln Asn Asp Ile Met Leu Leu Gln Leu Ser Arg
                85                  90                  95

Arg Val Arg Arg Asn Arg Asn Val Asn Pro Val Ala Leu Pro Arg Ala
            100             105                 110

Gln Glu Gly Leu Arg Pro Gly Thr Leu Cys Thr Val Ala Gly Trp Gly
            115             120                 125

Arg Val Ser Met Arg Arg Gly Thr Asp Thr Leu Arg Glu Val Gln Leu
    130             135                 140

Arg Val Gln Arg Asp Arg Gln Cys Leu Arg Ile Phe Gly Ser Tyr Asp
145             150                 155                     160

Pro Arg Arg Gln Ile Cys Val Gly Asp Arg Arg Glu Arg Lys Ala Ala
                165                 170                 175

Phe Lys Gly Asp Ser Gly Gly Pro Leu Leu Cys Asn Asn Val Ala His
            180                 185                 190

Gly Ile Val Ser Tyr Gly Lys Ser Ser Gly Val Pro Pro Glu Val Phe
        195                 200                 205

Thr Arg Val Ser Ser Phe Leu Pro Trp Ile Arg Thr Thr Met Arg
    210                 215                 220

( 2 ) INFORMATION FOR SEQ ID NO:42:

( i ) SEQUENCE CHARACTERISTICS:
( A ) LENGTH: 20 amino acids
( B ) TYPE: amino acid
( C ) STRANDEDNESS: single
( D ) TOPOLOGY: linear ( i i ) MOLECULE TYPE: peptide ( x i ) SEQUENCE DESCRIPTION: SEQ ID NO:42:

Lys Pro Gly Gln Thr Cys Ser Val Ala Gly Trp Gly Gln Thr Ala Pro
1               5                   10                  15

Leu Gly Lys Ser
            20

( 2 ) INFORMATION FOR SEQ ID NO:43:

( i ) SEQUENCE CHARACTERISTICS:
        ( A ) LENGTH: 20 amino acids
        ( B ) TYPE: amino acid
        ( C ) STRANDEDNESS: single
        ( D ) TOPOLOGY: linear ( i i ) MOLECULE TYPE: peptide ( x i ) SEQUENCE DESCRIPTION: SEQ ID NO:43:

```
Lys  Pro  Gln  Asp  Val  Cys  Tyr  Val  Ala  Gly  Trp  Gly  Arg  Met  Ala  Pro
1                   5                        10                       15
Met  Gly  Lys  Tyr
          20
```

( 2 ) INFORMATION FOR SEQ ID NO:44:

( i ) SEQUENCE CHARACTERISTICS:
        ( A ) LENGTH: 20 amino acids
        ( B ) TYPE: amino acid
        ( C ) STRANDEDNESS: single
        ( D ) TOPOLOGY: linear ( i i ) MOLECULE TYPE: peptide ( x i ) SEQUENCE DESCRIPTION: SEQ ID NO:44:

```
Glu  Ala  Gln  Thr  Arg  Cys  Gln  Val  Ala  Gly  Trp  Gly  Ser  Gln  Ser  Arg
1                   5                        10                       15
Ser  Gly  Gly  Arg
          20
```

( 2 ) INFORMATION FOR SEQ ID NO:45:

( i ) SEQUENCE CHARACTERISTICS:
        ( A ) LENGTH: 20 amino acids
        ( B ) TYPE: amino acid
        ( C ) STRANDEDNESS: single
        ( D ) TOPOLOGY: linear ( i i ) MOLECULE TYPE: peptide ( x i ) SEQUENCE DESCRIPTION: SEQ ID NO:45:

```
Gly  Asn  Gly  Val  Gln  Cys  Leu  Ala  Met  Gly  Trp  Gly  Leu  Leu  Gly  Arg
1                   5                        10                       15
Asn  Arg  Gly  Ile
          20
```

( 2 ) INFORMATION FOR SEQ ID NO:46:

( i ) SEQUENCE CHARACTERISTICS:
        ( A ) LENGTH: 20 amino acids
        ( B ) TYPE: amino acid
        ( C ) STRANDEDNESS: single
        ( D ) TOPOLOGY: linear ( i i ) MOLECULE TYPE: peptide ( x i ) SEQUENCE DESCRIPTION: SEQ ID NO:46:

```
Pro  His  Gly  Thr  Gln  Cys  Leu  Ala  Met  Gly  Trp  Gly  Arg  Val  Gly  Ala
1                   5                        10                       15
His  Pro  Pro  Pro
          20
```

( 2 ) INFORMATION FOR SEQ ID NO:47:

( i ) SEQUENCE CHARACTERISTICS:
        ( A ) LENGTH: 20 amino acids
        ( B ) TYPE: amino acid (C) STRANDEDNESS: single
(D) TOPOLOGY: linear (ii) MOLECULE TYPE: peptide (xi) SEQUENCE DESCRIPTION: SEQ ID NO:47:

Ala Ala Gly Thr Thr Cys Val Thr Thr Gly Trp Gly Leu Thr Arg Tyr
1               5                   10                  15

Thr Asn Ala Asn
         20

(2) INFORMATION FOR SEQ ID NO:48:

(i) SEQUENCE CHARACTERISTICS:
    (A) LENGTH: 21 amino acids
    (B) TYPE: amino acid
    (C) STRANDEDNESS: single
    (D) TOPOLOGY: linear (ii) MOLECULE TYPE: peptide (xi) SEQUENCE DESCRIPTION: SEQ ID NO:48:

Gly Ile Gly Lys Phe Leu His Ser Ala Lys Lys Phe Lys Ala Phe Val
1               5                   10                  15

Gly Glu Ile Met Asn
         20

(2) INFORMATION FOR SEQ ID NO:49:

(i) SEQUENCE CHARACTERISTICS:
    (A) LENGTH: 7 amino acids
    (B) TYPE: amino acid
    (C) STRANDEDNESS: single
    (D) TOPOLOGY: linear (ii) MOLECULE TYPE: peptide (xi) SEQUENCE DESCRIPTION: SEQ ID NO:49:

His Pro Gln Tyr Asn Pro Lys
1               5

(2) INFORMATION FOR SEQ ID NO:50:

(i) SEQUENCE CHARACTERISTICS:
    (A) LENGTH: 7 amino acids
    (B) TYPE: amino acid
    (C) STRANDEDNESS: single
    (D) TOPOLOGY: linear (ii) MOLECULE TYPE: peptide (xi) SEQUENCE DESCRIPTION: SEQ ID NO:50:

His Pro Gln Tyr Asn Pro Arg
1               5

(2) INFORMATION FOR SEQ ID NO:51:

(i) SEQUENCE CHARACTERISTICS:
    (A) LENGTH: 7 amino acids
    (B) TYPE: amino acid
    (C) STRANDEDNESS: single
    (D) TOPOLOGY: linear (ii) MOLECULE TYPE: peptide (xi) SEQUENCE DESCRIPTION: SEQ ID NO:51:

Tyr Pro Cys Tyr Asp Pro Ala
1               5

(2) INFORMATION FOR SEQ ID NO:52:

( i ) SEQUENCE CHARACTERISTICS:
    ( A ) LENGTH: 7 amino acids
    ( B ) TYPE: amino acid
    ( C ) STRANDEDNESS: single
    ( D ) TOPOLOGY: linear ( i i ) MOLECULE TYPE: peptide ( x i ) SEQUENCE DESCRIPTION: SEQ ID NO:52:

```
His  Pro  Ala  Tyr  Asn  Ala  Lys
1                   5
```

( 2 ) INFORMATION FOR SEQ ID NO:53:

( i ) SEQUENCE CHARACTERISTICS:
        ( A ) LENGTH: 7 amino acids
        ( B ) TYPE: amino acid
        ( C ) STRANDEDNESS: single
        ( D ) TOPOLOGY: linear ( i i ) MOLECULE TYPE: peptide ( x i ) SEQUENCE DESCRIPTION: SEQ ID NO:53:

```
His  Pro  Asp  Tyr  Asn  Gln  Arg
1                   5
```

( 2 ) INFORMATION FOR SEQ ID NO:54:

( i ) SEQUENCE CHARACTERISTICS:
        ( A ) LENGTH: 7 amino acids
        ( B ) TYPE: amino acid
        ( C ) STRANDEDNESS: single
        ( D ) TOPOLOGY: linear ( i i ) MOLECULE TYPE: peptide ( x i ) SEQUENCE DESCRIPTION: SEQ ID NO:54:

```
Tyr  Pro  Cys  Tyr  Asp  Glu  Tyr
1                   5
```

( 2 ) INFORMATION FOR SEQ ID NO:55:

( i ) SEQUENCE CHARACTERISTICS:
        ( A ) LENGTH: 7 amino acids
        ( B ) TYPE: amino acid
        ( C ) STRANDEDNESS: single
        ( D ) TOPOLOGY: linear ( i i ) MOLECULE TYPE: peptide ( x i ) SEQUENCE DESCRIPTION: SEQ ID NO:55:

```
His  Pro  Asp  Tyr  Asn  Pro  Lys
1                   5
```

( 2 ) INFORMATION FOR SEQ ID NO:56:

( i ) SEQUENCE CHARACTERISTICS:
        ( A ) LENGTH: 7 amino acids
        ( B ) TYPE: amino acid
        ( C ) STRANDEDNESS: single
        ( D ) TOPOLOGY: linear ( i i ) MOLECULE TYPE: peptide ( x i ) SEQUENCE DESCRIPTION: SEQ ID NO:56:

```
His  Pro  Asp  Tyr  Asn  Pro  Asp
1                   5
```

( 2 ) INFORMATION FOR SEQ ID NO:57:

( i ) SEQUENCE CHARACTERISTICS:

(A) LENGTH: 7 amino acids
        (B) TYPE: amino acid
        (C) STRANDEDNESS: single
        (D) TOPOLOGY: linear (ii) MOLECULE TYPE: peptide (xi) SEQUENCE DESCRIPTION: SEQ ID NO:57:

His Pro Asp Tyr Asn Ala Thr
    1               5

(2) INFORMATION FOR SEQ ID NO:58:

(i) SEQUENCE CHARACTERISTICS:
        (A) LENGTH: 7 amino acids
        (B) TYPE: amino acid
        (C) STRANDEDNESS: single
        (D) TOPOLOGY: linear (ii) MOLECULE TYPE: peptide (xi) SEQUENCE DESCRIPTION: SEQ ID NO:58:

His Pro Ala Tyr Asp Asp Lys
    1               5

(2) INFORMATION FOR SEQ ID NO:59:

(i) SEQUENCE CHARACTERISTICS:
        (A) LENGTH: 7 amino acids
        (B) TYPE: amino acid
        (C) STRANDEDNESS: single
        (D) TOPOLOGY: linear (ii) MOLECULE TYPE: peptide (xi) SEQUENCE DESCRIPTION: SEQ ID NO:59:

His Pro Ala Phe Asp Arg Lys
    1               5